(12) United States Patent
Seegert et al.

(10) Patent No.: US 7,629,147 B2
(45) Date of Patent: Dec. 8, 2009

(54) PEGYLATED SOLUBLE GP130-DIMERS USEFUL AS A MEDICAMENT

(75) Inventors: Dirk Seegert, Kiel (DE); Stefan Schreiber, Kiel (DE); Stefan Rose-John, Kiel (DE); Georg H. Watzig, Kiel (DE); Nikolaus Rahaus, Kiel (DE)

(73) Assignee: Conaris Research Institute AG, Kiel (DE)

(*) Notice: Subject to any disclaimer, the term of this patent is extended or adjusted under 35 U.S.C. 154(b) by 0 days.

(21) Appl. No.: 12/026,476

(22) Filed: Feb. 5, 2008

(65) Prior Publication Data

US 2008/0227155 A1 Sep. 18, 2008

Related U.S. Application Data

(62) Division of application No. 10/561,874, filed as application No. PCT/EP2004/006787 on Jun. 23, 2004.

(30) Foreign Application Priority Data

Jun. 23, 2003 (EP) .................. 03014049

(51) Int. Cl.
C12N 5/10 (2006.01)
C12N 15/12 (2006.01)
C12N 15/63 (2006.01)
(52) U.S. Cl. ............. 435/69.1; 435/252.3; 435/320.1; 435/325
(58) Field of Classification Search ............ None
See application file for complete search history.

(56) References Cited

U.S. PATENT DOCUMENTS

| 4,751,180 | A | 6/1988 | Cousens et al. |
|---|---|---|---|
| 5,783,672 | A | 7/1998 | Mosley et al. |
| 6,838,076 | B2 | 1/2005 | Patton et al. |
| 2007/0270334 | A1 | 11/2007 | Seegert et al. |

FOREIGN PATENT DOCUMENTS

| EP | 0442724 | A2 | 8/1991 |
|---|---|---|---|
| EP | 1148065 | * | 10/2001 |
| EP | 1148065 | A1 | 10/2001 |

OTHER PUBLICATIONS

Mikayama et al. Proc. Natl. Acad. Sci. USA vol. 90, pp. 10056-10060.*
Voet et al. Biochemistry John Wiley & Sons, Inc., pp. 126-128 and 228-234.*
Eck & Wilson in Goodman & Gilman's the Pharmacological Basis of Therapeutics, Ninth Edition, McGraw-Hill New York, 1996.*
Atreya, et al. Blockade of interleukin 6 trans signaling suppresses T-cell resistance against apoptosis in chronic intestinal inflammation: evidence in crohn disease and experimental colitis in vivo. Nat Med. May 2000;6(5):583-8.
Bitter, et al. Expression and Secretion Vectors for Yeast. Methods in Enzymology. 1987;153: 516-544.
Broglie, et al. Light-regulated expression of a pea ribulose-1,5-bisphosphate carboxylase small subunit gene in transformed plant cells. Science. May 25, 1984;224(4651):838-43.
Colbere-Garapin, et al. A new dominant hybrid selective marker for higher eukaryotic cells. J Mol Biol. Jul. 25, 1981;150(1):1-14.
Coruzzi, et al. Tissue-specific and light-regulated expression of a pea nuclear gene encoding the small subunit of ribulose-1,5-bisphosphate carboxylase. EMBO J. Aug 1984;3(8):1671-9.
Cunningham, et al. High-resolution epitope mapping of hGH-receptor interactions by alanine-scanning mutagenesis. Science. Jun. 2, 1989;244(4908):1081-5.
Cunningham, et al. Receptor and antibody epitopes in human growth hormone identified by homolog-scanning mutagenesis. Science. Mar. 10 1989;243(4896):1330-6.
Database UniProt Interleulin-6 receptor beta chain precursor. Feb. 1, 1995, HIBI: "Interleulin signal transducer" XP002322123 retrieved from EBI Database accession No. P40189 abstract.
Engelhard, et al. The insect tracheal system: a conduit for the systemic spread of Autographa californica M nuclear polyhedrosis virus. Proc Natl Acad Sci U S A. Apr. 12, 1994; 91(8): 3224-3227.
Fingl, et al. Chapter 1, General Principles, The Pharmocological Basis of Therapeutics, Goodman and Gilman, eds. Macmillan Publishing Co., New York, pp. 1 46 (1975).
Goodson, et al. Site-directed pegylation of recombinant interleukin-2 at its glycosylation site. Biotechnology (N Y). Apr 1990;8(4):343-6.
Grace, et al. Structural and biologic characterization of pegylated recombinant IFN-alpha2b. J Interferon Cytokine Res. Dec. 2001;21(12):1103-15.
Hartman, et al. Two dominant-acting selectable markers for gene transfer studies in mammalian cells. Proc Natl Acad Sci U S A. Nov 1988;85(21):8047-51.
Inoue, et al. A highly enhanced thrombopoietic activity by monomethoxy polyethylene glycol-modified recombinant human interleukin-6 J. Lab Clin. Med. 1994;124(4):529-36.
Katre, N. V Immunogenicity of recombinant IL-2 modified by covalent attachment of polyethylene glycol. J Immunol. Jan. 1, 1990;144(1):209-13.
Krause, et al. Rheumatoid arthritis synoviocyte survival is dependent on Stat3. J Immunol. Dec. 1, 2002;169(11):6610-6.
Levy, et al. What does Stat3 do? J Clin Invest. May 1, 2002; 109(9): 1143-1148.
Logan, et al. Adenovirus tripartite leader sequence enhances translation of mRNAs late after infection. Proc Natl Acad Sci U S A. Jun. 1984;81(12):3655-9.
Lowy, et al. Isolation of transforming DNA: cloning the hamster aprt gene. Cell. Dec. 1980;22(3):817-23.
Mikayama, et al. Molecular cloning and functional expression of a cDNA encoding glycosylation-inhibiting factor. Proc Natl Acad Sci U S A. Nov. 1, 1993;90(21):10056-10060.

(Continued)

*Primary Examiner*—Prema Mertz
(74) *Attorney, Agent, or Firm*—Wilson Sonsini Goodrich & Rosati

(57) ABSTRACT

A polypeptide-dimer comprising two soluble gp130 molecules is described, wherein at least one of said soluble gp130 molecules is covalently linked to polyethylene glycol. Furthermore, a pharmaceutical composition containing said dimer and various medical uses are described.

4 Claims, 9 Drawing Sheets

OTHER PUBLICATIONS

Müllberg, et al. IL-6 receptor independent stimulation of human gp130 by viral IL-6. J Immunol. May 1, 2000;164(9):4672-7.

Murry, L.E., Agrobacterium-Mediated plant transformation in McGraw Hill Yearbook of Science and Technology. McGraw Hill, New York, NY. 1992; 191-196.

Nishimoto, T. A new role of ran GTPase. Biochem Biophys Res Commun Sep. 7, 1999;262(3):571-4.

Nishimoto, et al. Anticytokine therapy in autoimmune diseases. Intern. Med. Feb. 1999; 38(2): 178-82.

Pepinsky, et al. Improved pharmacokinetic properties of a polyethylene glycol-modified form of interferon-beta-1a with preserved in vitro bioactivity. J Pharmacol Exp Ther. Jun. 2001;297(3):1059-66.

Pettit, et al. Structure-function studies of interleukin 15 using site-specific mutagenesis, polyethylene glycol conjugation, and homology modeling. J Biol Chem. Jan. 24, 1997;272(4):2312-8.

Rakemann, et al. The designer cytokine hyper-interleukin-6 is a potent activator of STAT3-dependent gene transcription in vivo and in vitro. J Biol Chem. Jan. 15, 1999;274(3):1257-66.

Rhodes, et al. Identification of MRF4: a new member of the muscle regulatory factor gene family. Genes Dev. Dec. 1989;3(12B):2050-61.

Rhodes, et al. Transformation of Maize by Electroporation of Embryos. (1995) Methods Mol. Biol. 55: 121 131.

Sambrook, J. Molecular Cloning: A Laboratory Manual. Cold Spring Harbor Laboratory Press, Cold Spring Harbor, NY(1989). (Cover pages and table of contents pages only).

Scharf, et al. Heat stress promoters and transcription factors. Results Probl Cell Differ. 1994;20:125-62.

Suzuki, et al. CIS3/SOCS3/SSI3 plays a negative regulatory role in STAT3 activation and intestinal inflammation. J Exp Med. Feb. 19, 2001;193(4):471-81.

Takamatsu, et al. Expression of bacterial chloramphenicol acetyltransferase gene in tobacco plants mediated by TMV-RNA. EMBO J. Feb. 1987;6(2):307-11.

Tang, et al. Studies on the PEGylation of Protein at a Specific Site: Sulfhydryl-PEGylation of 97Cys-IFN-gamma. Sheng Wu Hua Xue Yu Sheng Wu Wu Li Xue Bao (Shanghai). 1996;28(3):312-315. (in Chinese with English abstract).

Tsunoda, et al. Selective enhancement of thrombopoietic activity of PEGylated interleukin 6 by a simple procedure using a reversible amino-protective reagent. Br. J Haematol. 2001;112(1):181-8.

Turkson, et al. STAT proteins: novel molecular targets for cancer drug discovery. Oncogene. Dec. 27, 2000;19(56):6613-26.

Voet, et al. Biochemistry. John Wiley & Sons, Inc. 1990; 126-128 and 228-234.

Wigler, et al. Transfer of purified herpes virus thymidine kinase gene to cultured mouse cells. Cell. May 1977;11(1):223-32.

Wigler, et al. Transformation of mammalian cells with an amplifiable dominant-acting gene. Proc Natl Acad Sci U S A. Jun. 1980;77(6):3567-70.

Winter, et al. The expression of heat shock protein and cognate genes during plant development. Results Probl Cell Differ. 1991;17:85-105.

Yoshizaki, et al. Interleukin-6 in autoimmune disorders. Semin Immunol Jun. 1992;4(3):155-66.

Youngster, et al. Structure, biology, and therapeutic implications of pegylated interferon alpha-2b. Curr Pharm Des. 2002;8(24):2139-57.

* cited by examiner

```
atgttgacgttgcagacttggggtagtgcaagccttgtttattttcctcaccactgaatct
 M  L  T  L  Q  T  W  V  V  Q  A  L  F  I  F  L  T  T  E  S
acaggtgaacttctagatccatgtggttatatcagtcctgaatctccagttgtacaactt
 T  G  E  L  L  D  P  C  G  Y  I  S  P  E  S  P  V  V  Q  L
cattctaatttcactgcagtttgtgtgctaaaggaaaaatgtatggattatttcatgta
 H  S  N  F  T  A  V  C  V  L  K  E  K  C  M  D  Y  F  H  V
aatgctaattacattgtctggaaaacaaaccatttactattcctaaggagcaatatact
 N  A  N  Y  I  V  W  K  T  N  H  F  T  I  P  K  E  Q  Y  T
atcataaacagaacagcatccagtgtcacctttacagatatagcttcattaaatattcag
 I  I  N  R  T  A  S  S  V  T  F  T  D  I  A  S  L  N  I  Q
ctcacttgcaacattcttacattcggacagcttgaacagaatgtttatggaatcacaata
 L  T  C  N  I  L  T  F  G  Q  L  E  Q  N  V  Y  G  I  T  I
atttcaggcttgcctccagaaaaacctaaaaatttgagttgcattgtgaacgaggggaag
 I  S  G  L  P  P  E  K  P  K  N  L  S  C  I  V  N  E  G  K
aaaatgaggtgtgagtgggatggtggaagggaaacacacttggagacaaacttcacttta
 K  M  R  C  E  W  D  G  G  R  E  T  H  L  E  T  N  F  T  L
aaatctgaatgggcaacacacaagtttgctgattgcaaagcaaaacgtgacacccccacc
 K  S  E  W  A  T  H  K  F  A  D  C  K  A  K  R  D  T  P  T
tcatgcactgttgattattctactgtgtatttgtcaacattgaagtctgggtagaagca
 S  C  T  V  D  Y  S  T  V  Y  F  V  N  I  E  V  W  V  E  A
gagaatgcccttgggaaggttacatcagatcatatcaattttgatcctgtatataaagtg
 E  N  A  L  G  K  V  T  S  D  H  I  N  F  D  P  V  Y  K  V
aagcccaatccgccacataatttatcagtgatcaactcagaggaactgtctagtatctta
 K  P  N  P  P  H  N  L  S  V  I  N  S  E  E  L  S  S  I  L
aaattgacatggaccaacccaagtattaagagtgttataatactaaaatataacattcaa
 K  L  T  W  T  N  P  S  I  K  S  V  I  I  L  K  Y  N  I  Q
tataggaccaaagatgcctcaacttggagccagattcctcctgaagacacagcatccacc
 Y  R  T  K  D  A  S  T  W  S  Q  I  P  P  E  D  T  A  S  T
cgatcttcattcactgtccaagaccttaaaccttttacagaatatgtgtttaggattcgc
 R  S  S  F  T  V  Q  D  L  K  P  F  T  E  Y  V  F  R  I  R
tgtatgaaggaagatggtaagggatactggagtgactggagtgaagaagcaagtgggatc
 C  M  K  E  D  G  K  G  Y  W  S  D  W  S  E  E  A  S  G  I
acctatgaagatagacca
 T  Y  E  D  R  P
```

Figure 2

```
atgtgctggttcaagttgtggtctctcttgctggtcggttcactgctggtatctggaacg
 M  C  W  F  K  L  W  S  L  L  L  V  G  S  L  L  V  S  G  T
cggggcaagttgccggacgcccccgagtttgaaaaggatcttctcattcagagactcaat
 R  G  K  L  P  D  A  P  E  F  E  K  D  L  L  I  Q  R  L  N
tggatgctatgggtgatcgatgaatgcttccgcgacctctgttaccgtaccggcatctgc
 W  M  L  W  V  I  D  E  C  F  R  D  L  C  Y  R  T  G  I  C
aagggtattctagagcccgctgctattttcatctgaaactaccagccatcaacgatact
 K  G  I  L  E  P  A  A  I  F  H  L  K  L  P  A  I  N  D  T
gatcactgcggttaataggatttaatgagactagctgccttaaaaagctcgccgatggc
 D  H  C  G  L  I  G  F  N  E  T  S  C  L  K  K  L  A  D  G
tttttgaattcgaggtgttgtttaagttttaacgacggagtttggaaaatcagtgata
 F  F  E  F  E  V  L  F  K  F  L  T  T  E  F  G  K  S  V  I
aacgtggacgtcatggagcttctgacgaagaccttaggatgggacatacaggaagagctc
 N  V  D  V  M  E  L  L  T  K  L  G  W  D  I  Q  E  E  L
aataagctgactaagacgcactacagtccacccaaatttgaccgcggtctattagggagg
 N  K  L  T  K  T  H  Y  S  P  P  K  F  D  R  G  L  L  G  R
cttcagggacttaagtattgggtgagacactttgcttcgttttatgttctgagtgcaatg
 L  Q  G  L  K  Y  W  V  R  H  F  A  S  F  Y  V  L  S  A  M
gaaaagtttgcaggtcaagcggtgcgtgttttggactctatcccagacgtgactcctgac
 E  K  F  A  G  Q  A  V  R  V  L  D  S  I  P  D  V  T  P  D
gtccacgataagtaa
 V  H  D  K  -
```

Figure 3

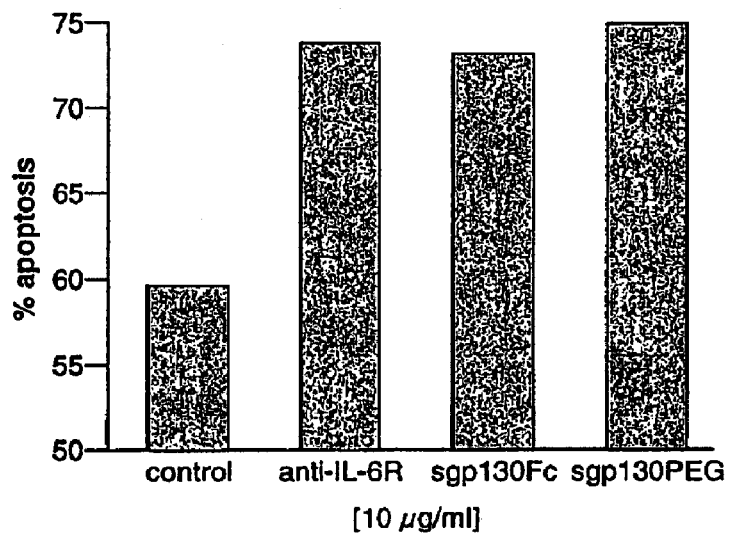

```
atggaacttctagatccatgtggttatatcagtcctgaatctccagttgtacaactt
 M  E  L  L  D  P  C  G  Y  I  S  P  E  S  P  V  V  Q  L
cattctaatttcactgcagtttgtgtgctaaaggaaaaatgtatggattatttcatgta
 H  S  N  F  T  A  V  C  V  L  K  E  K  C  M  D  Y  F  H  V
aatgctaattacattgtctggaaaacaaaccatttactattcctaaggagcaatatact
 N  A  N  Y  I  V  W  K  T  N  H  F  T  I  P  K  E  Q  Y  T
atcataaacagaacagcatccagtgtcacctttacagatatagcttcattaaatattcag
 I  I  N  R  T  A  S  S  V  T  F  T  D  I  A  S  L  N  I  Q
ctcacttgcaacattcttacattcggacagcttgaacagaatgtttatggaatcacaata
 L  T  C  N  I  L  T  F  G  Q  L  E  Q  N  V  Y  G  I  T  I
atttcaggcttgcctccagaaaaacctaaaaatttgagttgcattgtgaacgaggggaag
 I  S  G  L  P  P  E  K  P  K  N  L  S  C  I  V  N  E  G  K
aaaatgaggtgtgagtgggatggtggaagggaaacacacttggagacaaacttcacttta
 K  M  R  C  E  W  D  G  G  R  E  T  H  L  E  T  N  F  T  L
aaatctgaatgggcaacacacaagtttgctgattgcaaagcaaaacgtgacaccccacc
 K  S  E  W  A  T  H  K  F  A  D  C  K  A  K  R  D  T  P  T
tcatgcactgttgattattctactgtgtatttgtcaacattgaagtctgggtagaagca
 S  C  T  V  D  Y  S  T  V  Y  F  V  N  I  E  V  W  V  E  A
gagaatgcccttgggaaggttacatcagatcatatcaattttgatcctgtatataaagtg
 E  N  A  L  G  K  V  T  S  D  H  I  N  F  D  P  V  Y  K  V
aagcccaatccgccacataatttatcagtgatcaactcagaggaactgtctagtatctta
 K  P  N  P  P  H  N  L  S  V  I  N  S  E  E  L  S  S  I  L
aaattgacatggaccaacccaagtattaagagtgttataatactaaaatataacattcaa
 K  L  T  W  T  N  P  S  I  K  S  V  I  I  L  K  Y  N  I  Q
tataggaccaaagatgcctcaacttggagccagattcctcctgaagacacagcatccacc
 Y  R  T  K  D  A  S  T  W  S  Q  I  P  P  E  D  T  A  S  T
cgatcttcattcactgtccaagaccttaaaccttttacagaatatgtgtttaggattcgc
 R  S  S  F  T  V  Q  D  L  K  P  F  T  E  Y  V  F  R  I  R
tgtatgaaggaagatggtaagggatactggagtgactggagtgaagaagcaagtgggatc
 C  M  K  E  D  G  K  G  Y  W  S  D  W  S  E  E  A  S  G  I
acctatgaagatagacca
 T  Y  E  D  R  P
```

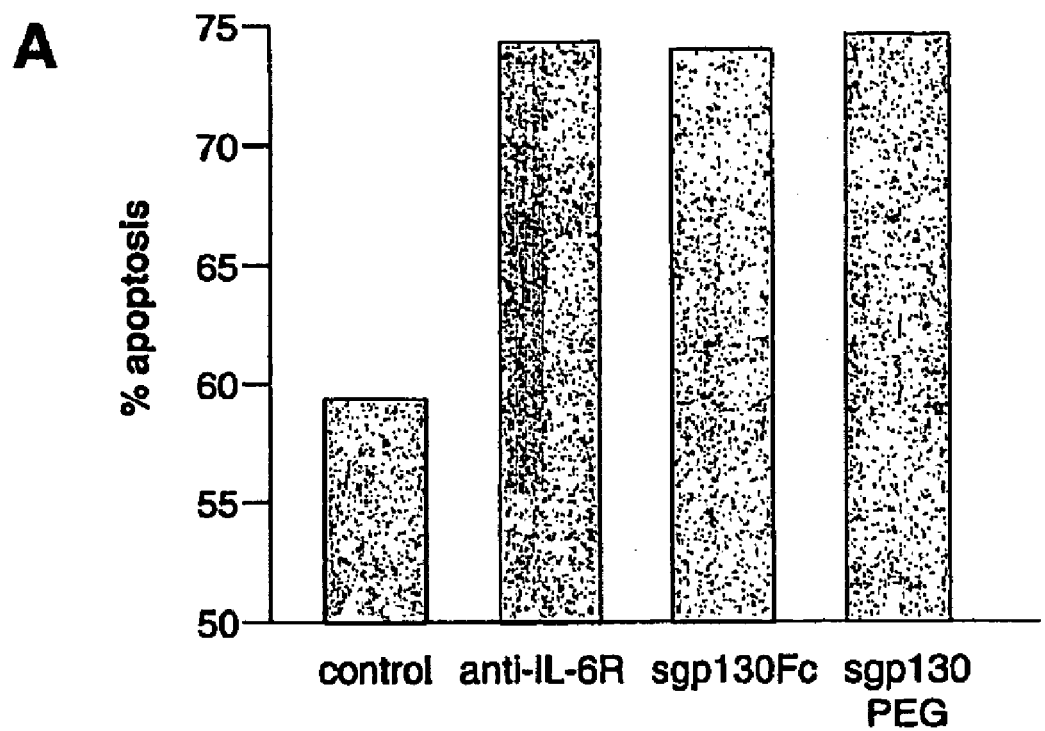
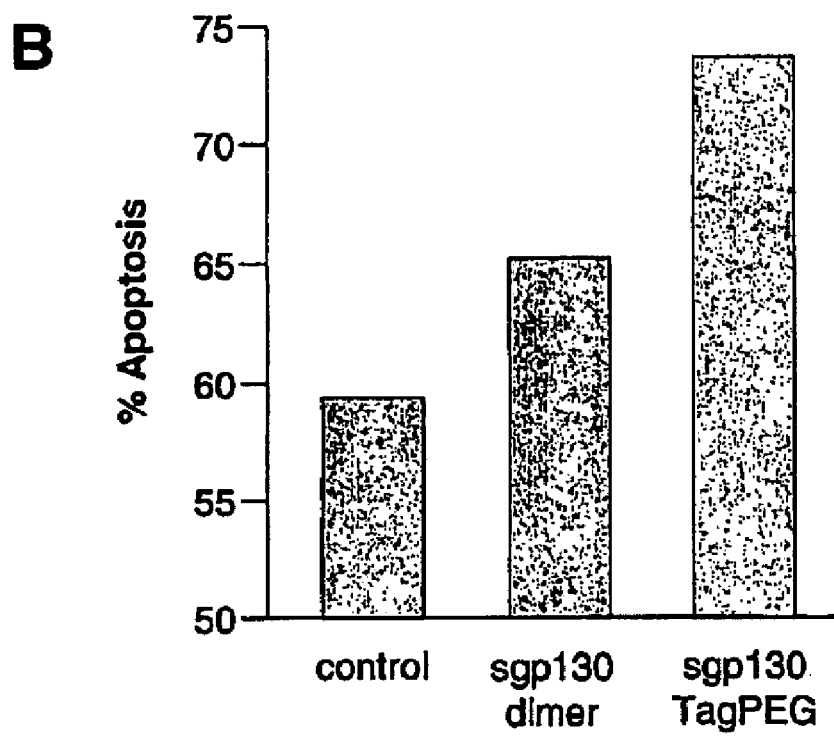
Fig. 8

Fig. 9
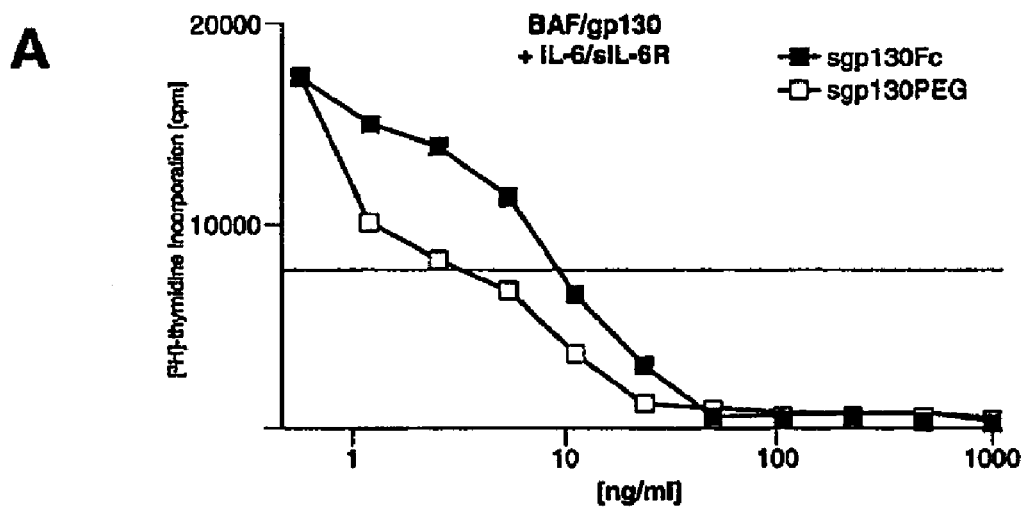
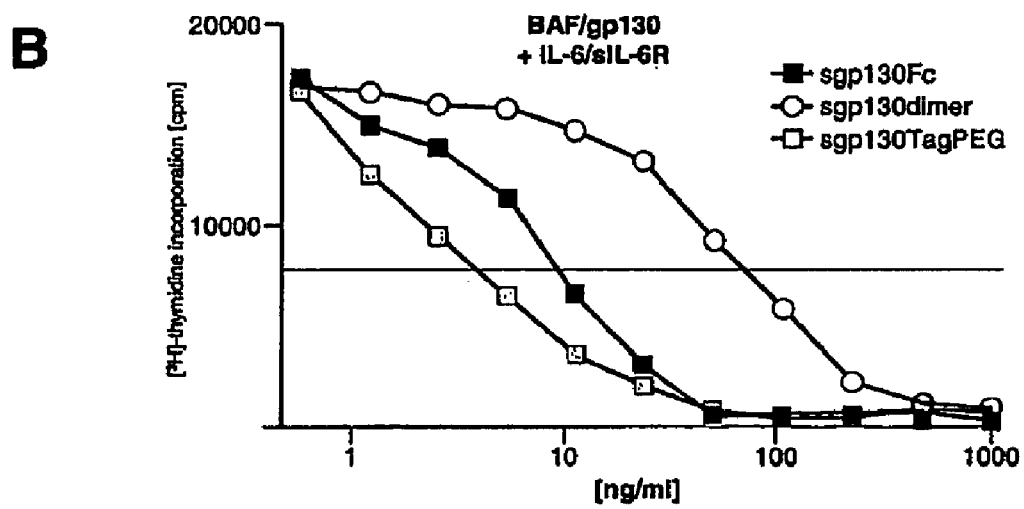

SEQUENCE LISTING

<160> NUMBER OF SEQ ID NOS: 8

<210> SEQ ID NO 1
<211> LENGTH: 978
<212> TYPE: DNA
<213> ORGANISM: Homo sapiens
<220> FEATURE:
<221> NAME/KEY: CDS
<222> LOCATION: (1)..(978)

<400> SEQUENCE: 1

```
atg ttg acg ttg cag act tgg gta gtg caa gcc ttg ttt att ttc ctc      48
Met Leu Thr Leu Gln Thr Trp Val Val Gln Ala Leu Phe Ile Phe Leu
1               5                   10                  15 acc act gaa tct aca ggt gaa ctt cta gat cca tgt ggt tat atc agt      96
Thr Thr Glu Ser Thr Gly Glu Leu Leu Asp Pro Cys Gly Tyr Ile Ser
        20                  25                  30 cct gaa tct cca gtt gta caa ctt cat tct aat ttc act gca gtt tgt     144
Pro Glu Ser Pro Val Val Gln Leu His Ser Asn Phe Thr Ala Val Cys
    35                  40                  45 gtg cta aag gaa aaa tgt atg gat tat ttt cat gta aat gct aat tac     192
Val Leu Lys Glu Lys Cys Met Asp Tyr Phe His Val Asn Ala Asn Tyr
50                  55                  60 att gtc tgg aaa aca aac cat ttt act att cct aag gag caa tat act     240
Ile Val Trp Lys Thr Asn His Phe Thr Ile Pro Lys Glu Gln Tyr Thr
65                  70                  75                  80 atc ata aac aga aca gca tcc agt gtc acc ttt aca gat ata gct tca     288
Ile Ile Asn Arg Thr Ala Ser Ser Val Thr Phe Thr Asp Ile Ala Ser
                85                  90                  95 tta aat att cag ctc act tgc aac att ctt aca ttc gga cag ctt gaa     336
Leu Asn Ile Gln Leu Thr Cys Asn Ile Leu Thr Phe Gly Gln Leu Glu
            100                 105                 110 cag aat gtt tat gga atc aca ata att tca ggc ttg cct cca gaa aaa     384
Gln Asn Val Tyr Gly Ile Thr Ile Ile Ser Gly Leu Pro Pro Glu Lys
        115                 120                 125 cct aaa aat ttg agt tgc att gtg aac gag ggg aag aaa atg agg tgt     432
Pro Lys Asn Leu Ser Cys Ile Val Asn Glu Gly Lys Lys Met Arg Cys
    130                 135                 140 gag tgg gat ggt gga agg gaa aca cac ttg gag aca aac ttc act tta     480
Glu Trp Asp Gly Gly Arg Glu Thr His Leu Glu Thr Asn Phe Thr Leu
145                 150                 155                 160 aaa tct gaa tgg gca aca cac aag ttt gct gat tgc aaa gca aaa cgt     528
Lys Ser Glu Trp Ala Thr His Lys Phe Ala Asp Cys Lys Ala Lys Arg
                165                 170                 175 gac acc ccc acc tca tgc act gtt gat tat tct act gtg tat ttt gtc     576
Asp Thr Pro Thr Ser Cys Thr Val Asp Tyr Ser Thr Val Tyr Phe Val
            180                 185                 190 aac att gaa gtc tgg gta gaa gca gag aat gcc ctt ggg aag gtt aca     624
Asn Ile Glu Val Trp Val Glu Ala Glu Asn Ala Leu Gly Lys Val Thr
```

-continued

```
                195                 200                 205
tca gat cat atc aat ttt gat cct gta tat aaa gtg aag ccc aat ccg      672
Ser Asp His Ile Asn Phe Asp Pro Val Tyr Lys Val Lys Pro Asn Pro
210                 215                 220 cca cat aat tta tca gtg atc aac tca gag gaa ctg tct agt atc tta      720
Pro His Asn Leu Ser Val Ile Asn Ser Glu Glu Leu Ser Ser Ile Leu
225                 230                 235                 240 aaa ttg aca tgg acc aac cca agt att aag agt gtt ata ata cta aaa      768
Lys Leu Thr Trp Thr Asn Pro Ser Ile Lys Ser Val Ile Ile Leu Lys
245                 250                 255 tat aac att caa tat agg acc aaa gat gcc tca act tgg agc cag att      816
Tyr Asn Ile Gln Tyr Arg Thr Lys Asp Ala Ser Thr Trp Ser Gln Ile
260                 265                 270 cct cct gaa gac aca gca tcc acc cga tct tca ttc act gtc caa gac      864
Pro Pro Glu Asp Thr Ala Ser Thr Arg Ser Ser Phe Thr Val Gln Asp
275                 280                 285 ctt aaa cct ttt aca gaa tat gtg ttt agg att cgc tgt atg aag gaa      912
Leu Lys Pro Phe Thr Glu Tyr Val Phe Arg Ile Arg Cys Met Lys Glu
290                 295                 300 gat ggt aag gga tac tgg agt gac tgg agt gaa gaa gca agt ggg atc      960
Asp Gly Lys Gly Tyr Trp Ser Asp Trp Ser Glu Glu Ala Ser Gly Ile
305                 310                 315                 320 acc tat gaa gat aga cca                                              978
Thr Tyr Glu Asp Arg Pro
325

<210> SEQ ID NO 2
<211> LENGTH: 326
<212> TYPE: PRT
<213> ORGANISM: Homo sapiens

<400> SEQUENCE: 2

Met Leu Thr Leu Gln Thr Trp Val Val Gln Ala Leu Phe Ile Phe Leu
1               5                   10                  15

Thr Thr Glu Ser Thr Gly Glu Leu Leu Asp Pro Cys Gly Tyr Ile Ser
            20                  25                  30

Pro Glu Ser Pro Val Val Gln Leu His Ser Asn Phe Thr Ala Val Cys
        35                  40                  45

Val Leu Lys Glu Lys Cys Met Asp Tyr Phe His Val Asn Ala Asn Tyr
    50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
```

-continued

```
                        195                 200                 205

Ser Asp His Ile Asn Phe Asp Pro Val Tyr Lys Val Lys Pro Asn Pro
210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
245                 250                 255

Tyr Asn Ile Gln Tyr Arg Thr Lys Asp Ala Ser Thr Trp Ser Gln Ile
260                 265                 270

Pro Pro Glu Asp Thr Ala Ser Thr Arg Ser Ser Phe Thr Val Gln Asp
275                 280                 285

Leu Lys Pro Phe Thr Glu Tyr Val Phe Arg Ile Arg Cys Met Lys Glu
290                 295                 300

Asp Gly Lys Gly Tyr Trp Ser Asp Trp Ser Glu Ala Ser Gly Ile
305                 310                 315                 320

Thr Tyr Glu Asp Arg Pro
325

<210> SEQ ID NO 3
<211> LENGTH: 615
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(612)

<400> SEQUENCE: 3 atg tgc tgg ttc aag ttg tgg tct ctc ttg ctg gtc ggt tca ctg ctg        48
Met Cys Trp Phe Lys Leu Trp Ser Leu Leu Leu Val Gly Ser Leu Leu
1               5                   10                  15 gta tct gga acg cgg ggc aag ttg ccg gac gcc ccc gag ttt gaa aag        96
Val Ser Gly Thr Arg Gly Lys Leu Pro Asp Ala Pro Glu Phe Glu Lys
            20                  25                  30 gat ctt ctc att cag aga ctc aat tgg atg cta tgg gtg atc gat gaa       144
Asp Leu Leu Ile Gln Arg Leu Asn Trp Met Leu Trp Val Ile Asp Glu
        35                  40                  45 tgc ttc cgc gac ctc tgt tac cgt acc ggc atc tgc aag ggt att cta       192
Cys Phe Arg Asp Leu Cys Tyr Arg Thr Gly Ile Cys Lys Gly Ile Leu
    50                  55                  60 gag ccc gct gct att ttt cat ctg aaa cta cca gcc atc aac gat act       240
Glu Pro Ala Ala Ile Phe His Leu Lys Leu Pro Ala Ile Asn Asp Thr
65                  70                  75                  80 gat cac tgc ggg tta ata gga ttt aat gag act agc tgc ctt aaa aag       288
Asp His Cys Gly Leu Ile Gly Phe Asn Glu Thr Ser Cys Leu Lys Lys
                85                  90                  95 ctc gcc gat ggc ttt ttt gaa ttc gag gtg ttg ttt aag ttt tta acg       336
Leu Ala Asp Gly Phe Phe Glu Phe Glu Val Leu Phe Lys Phe Leu Thr
            100                 105                 110 acg gag ttt gga aaa tca gtg ata aac gtg gac gtc atg gag ctt ctg       384
Thr Glu Phe Gly Lys Ser Val Ile Asn Val Asp Val Met Glu Leu Leu
        115                 120                 125 acg aag acc tta gga tgg gac ata cag gaa gag ctc aat aag ctg act       432
Thr Lys Thr Leu Gly Trp Asp Ile Gln Glu Glu Leu Asn Lys Leu Thr
    130                 135                 140 aag acg cac tac agt cca ccc aaa ttt gac cgc ggt cta tta ggg agg       480
Lys Thr His Tyr Ser Pro Pro Lys Phe Asp Arg Gly Leu Leu Gly Arg
145                 150                 155                 160
```

```
ctt cag gga ctt aag tat tgg gtg aga cac ttt gct tcg ttt tat gtt      528
Leu Gln Gly Leu Lys Tyr Trp Val Arg His Phe Ala Ser Phe Tyr Val
165                 170                 175 ctg agt gca atg gaa aag ttt gca ggt caa gcg gtg cgt gtt ttg gac      576
Leu Ser Ala Met Glu Lys Phe Ala Gly Gln Ala Val Arg Val Leu Asp
180                 185                 190 tct atc cca gac gtg act cct gac gtc cac gat aag taa                  615
Ser Ile Pro Asp Val Thr Pro Asp Val His Asp Lys
195                 200

<210> SEQ ID NO 4
<211> LENGTH: 204
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Cys Trp Phe Lys Leu Trp Ser Leu Leu Val Gly Ser Leu Leu
1               5                   10                  15

Val Ser Gly Thr Arg Gly Lys Leu Pro Asp Ala Pro Glu Phe Glu Lys
20                  25                  30

Asp Leu Leu Ile Gln Arg Leu Asn Trp Met Leu Trp Val Ile Asp Glu
35                  40                  45

Cys Phe Arg Asp Leu Cys Tyr Arg Thr Gly Ile Cys Lys Gly Ile Leu
50                  55                  60

Glu Pro Ala Ala Ile Phe His Leu Lys Leu Pro Ala Ile Asn Asp Thr
65                  70                  75                  80

Asp His Cys Gly Leu Ile Gly Phe Asn Glu Thr Ser Cys Leu Lys Lys
85                  90                  95

Leu Ala Asp Gly Phe Phe Glu Phe Glu Val Leu Phe Lys Phe Leu Thr
100                 105                 110

Thr Glu Phe Gly Lys Ser Val Ile Asn Val Asp Val Met Glu Leu Leu
115                 120                 125

Thr Lys Thr Leu Gly Trp Asp Ile Gln Glu Glu Leu Asn Lys Leu Thr
130                 135                 140

Lys Thr His Tyr Ser Pro Pro Lys Phe Asp Arg Gly Leu Leu Gly Arg
145                 150                 155                 160

Leu Gln Gly Leu Lys Tyr Trp Val Arg His Phe Ala Ser Phe Tyr Val
165                 170                 175

Leu Ser Ala Met Glu Lys Phe Ala Gly Gln Ala Val Arg Val Leu Asp
180                 185                 190

Ser Ile Pro Asp Val Thr Pro Asp Val His Asp Lys
195                 200

<210> SEQ ID NO 5
<211> LENGTH: 915
<212> TYPE: DNA
<213> ORGANISM: Homo sapiens
<220> FEATURE:
<221> NAME/KEY: CDS
<222> LOCATION: (1)..(915)

<400> SEQUENCE: 5 atg gaa ctt cta gat cca tgt ggt tat atc agt cct gaa tct cca gtt      48
Met Glu Leu Leu Asp Pro Cys Gly Tyr Ile Ser Pro Glu Ser Pro Val
1               5                   10                  15 gta caa ctt cat tct aat ttc act gca gtt tgt gtg cta aag gaa aaa      96
```

```
Val Gln Leu His Ser Asn Phe Thr Ala Val Cys Val Leu Lys Glu Lys
 20              25                  30 tgt atg gat tat ttt cat gta aat gct aat tac att gtc tgg aaa aca    144
Cys Met Asp Tyr Phe His Val Asn Ala Asn Tyr Ile Val Trp Lys Thr
 35              40                  45 aac cat ttt act att cct aag gag caa tat act atc ata aac aga aca    192
Asn His Phe Thr Ile Pro Lys Glu Gln Tyr Thr Ile Ile Asn Arg Thr
 50              55                  60 gca tcc agt gtc acc ttt aca gat ata gct tca tta aat att cag ctc    240
Ala Ser Ser Val Thr Phe Thr Asp Ile Ala Ser Leu Asn Ile Gln Leu
 65              70                  75                  80 act tgc aac att ctt aca ttc gga cag ctt gaa cag aat gtt tat gga    288
Thr Cys Asn Ile Leu Thr Phe Gly Gln Leu Glu Gln Asn Val Tyr Gly
 85              90                  95 atc aca ata att tca ggc ttg cct cca gaa aaa cct aaa aat ttg agt    336
Ile Thr Ile Ile Ser Gly Leu Pro Pro Glu Lys Pro Lys Asn Leu Ser
100             105                 110 tgc att gtg aac gag ggg aag aaa atg agg tgt gag tgg gat ggt gga    384
Cys Ile Val Asn Glu Gly Lys Lys Met Arg Cys Glu Trp Asp Gly Gly
115             120                 125 agg gaa aca cac ttg gag aca aac ttc act tta aaa tct gaa tgg gca    432
Arg Glu Thr His Leu Glu Thr Asn Phe Thr Leu Lys Ser Glu Trp Ala
130             135                 140 aca cac aag ttt gct gat tgc aaa gca aaa cgt gac acc ccc acc tca    480
Thr His Lys Phe Ala Asp Cys Lys Ala Lys Arg Asp Thr Pro Thr Ser
145             150                 155                 160 tgc act gtt gat tat tct act gtg tat ttt gtc aac att gaa gtc tgg    528
Cys Thr Val Asp Tyr Ser Thr Val Tyr Phe Val Asn Ile Glu Val Trp
165             170                 175 gta gaa gca gag aat gcc ctt ggg aag gtt aca tca gat cat atc aat    576
Val Glu Ala Glu Asn Ala Leu Gly Lys Val Thr Ser Asp His Ile Asn
180             185                 190 ttt gat cct gta tat aaa gtg aag ccc aat ccg cca cat aat tta tca    624
Phe Asp Pro Val Tyr Lys Val Lys Pro Asn Pro Pro His Asn Leu Ser
195             200                 205 gtg atc aac tca gag gaa ctg tct agt atc tta aaa ttg aca tgg acc    672
Val Ile Asn Ser Glu Glu Leu Ser Ser Ile Leu Lys Leu Thr Trp Thr
210             215                 220 aac cca agt att aag agt gtt ata ata cta aaa tat aac att caa tat    720
Asn Pro Ser Ile Lys Ser Val Ile Ile Leu Lys Tyr Asn Ile Gln Tyr
225             230                 235                 240 agg acc aaa gat gcc tca act tgg agc cag att cct cct gaa gac aca    768
Arg Thr Lys Asp Ala Ser Thr Trp Ser Gln Ile Pro Pro Glu Asp Thr
245             250                 255 gca tcc acc cga tct tca ttc act gtc caa gac ctt aaa cct ttt aca    816
Ala Ser Thr Arg Ser Ser Phe Thr Val Gln Asp Leu Lys Pro Phe Thr
260             265                 270 gaa tat gtg ttt agg att cgc tgt atg aag gaa gat ggt aag gga tac    864
Glu Tyr Val Phe Arg Ile Arg Cys Met Lys Glu Asp Gly Lys Gly Tyr
275             280                 285 tgg agt gac tgg agt gaa gaa gca agt ggg atc acc tat gaa gat aga    912
Trp Ser Asp Trp Ser Glu Glu Ala Ser Gly Ile Thr Tyr Glu Asp Arg
290             295                 300 cca                                                                915
Pro
305

<210> SEQ ID NO 6
<211> LENGTH: 305
<212> TYPE: PRT
```

<213> ORGANISM: Homo sapiens

<400> SEQUENCE: 6

```
Met Glu Leu Leu Asp Pro Cys Gly Tyr Ile Ser Pro Glu Ser Pro Val
1               5                   10                  15

Val Gln Leu His Ser Asn Phe Thr Ala Val Cys Val Leu Lys Glu Lys
            20                  25                  30

Cys Met Asp Tyr Phe His Val Asn Ala Asn Tyr Ile Val Trp Lys Thr
        35                  40                  45

Asn His Phe Thr Ile Pro Lys Glu Gln Tyr Thr Ile Asn Arg Thr
    50                  55                  60

Ala Ser Ser Val Thr Phe Thr Asp Ile Ala Ser Leu Asn Ile Gln Leu
65                  70                  75                  80

Thr Cys Asn Ile Leu Thr Phe Gly Gln Leu Glu Gln Asn Val Tyr Gly
            85                  90                  95

Ile Thr Ile Ile Ser Gly Leu Pro Pro Glu Lys Pro Lys Asn Leu Ser
        100                 105                 110

Cys Ile Val Asn Glu Gly Lys Lys Met Arg Cys Glu Trp Asp Gly Gly
    115                 120                 125

Arg Glu Thr His Leu Glu Thr Asn Phe Thr Leu Lys Ser Glu Trp Ala
130                 135                 140

Thr His Lys Phe Ala Asp Cys Lys Ala Lys Arg Asp Thr Pro Thr Ser
145                 150                 155                 160

Cys Thr Val Asp Tyr Ser Thr Val Tyr Phe Val Asn Ile Glu Val Trp
            165                 170                 175

Val Glu Ala Glu Asn Ala Leu Gly Lys Val Thr Ser Asp His Ile Asn
        180                 185                 190

Phe Asp Pro Val Tyr Lys Val Lys Pro Asn Pro Pro His Asn Leu Ser
    195                 200                 205

Val Ile Asn Ser Glu Glu Leu Ser Ser Ile Leu Lys Leu Thr Trp Thr
210                 215                 220

Asn Pro Ser Ile Lys Ser Val Ile Ile Leu Lys Tyr Asn Ile Gln Tyr
225                 230                 235                 240

Arg Thr Lys Asp Ala Ser Thr Trp Ser Gln Ile Pro Pro Glu Asp Thr
            245                 250                 255

Ala Ser Thr Arg Ser Ser Phe Thr Val Gln Asp Leu Lys Pro Phe Thr
        260                 265                 270

Glu Tyr Val Phe Arg Ile Arg Cys Met Lys Glu Asp Gly Lys Gly Tyr
    275                 280                 285

Trp Ser Asp Trp Ser Glu Glu Ala Ser Gly Ile Thr Tyr Glu Asp Arg
290                 295                 300

Pro
305
```

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic 6xHis tag

<400> SEQUENCE: 7

```
His His His His His His
1               5
```

```
<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag
<220> FEATURE:
<221> NAME/KEY: MOD_RES
<222> LOCATION: (5)..(6)
<223> OTHER INFORMATION: May or may not be present

<400> SEQUENCE: 8

His His His His His His
1               5
```

US 7,629,147 B2

PEGYLATED SOLUBLE GP130-DIMERS USEFUL AS A MEDICAMENT

CROSS-REFERENCE

This application is a divisional application of U.S. Ser. No. 10/561,874, filed on Apr. 25, 2007, which is a national phase filing of Application No. PCT/EP04/06787, filed on Jun. 23, 2004, which claims the benefit of priority of European Application EP 03014049.5, filed Jun. 23, 2003, which are incorporated herein by reference in their entirety.

FIELD OF THE INVENTION

The present invention relates to a polypeptide-dimer comprising two soluble gp130 molecules, wherein at least one of said soluble gp130 molecules is covalently linked to polyethylene glycol. The present invention also relates to a pharmaceutical composition containing said dimer and various medical uses.

BACKGROUND

The pleiotropic cytokine interleukin-6 (IL-6) shows a wide spectrum of biological functions among which stimulation of B cells and induction of acute phase protein synthesis in liver are mostly notable. IL-6 exerts its activity on target cells via binding to an IL-6 specific surface receptor ("IL-6R" or "gp80"). This receptor/ligand complex facilitates homodimerization of gp130, the second subunit of the IL-6 receptor complex. Dimerization of gp130 results in transduction of an IL-6 signal. Soluble forms of the IL-6R (sIL-6R) which are generated by two mechanisms (alternative splicing and shedding) are also able to trigger gp130 dimerization and signalling when complexed with IL-6.

Since the cytoplasmic portion of the IL-6R does not contribute to signal transduction, signalling by a gp130 homodimer can be induced by IL-6 in complex with membrane bound or soluble IL-6R. The presence of sIL-6R, however, leads to sensitization of IL-6 responsive cells towards the ligand, as described previously for human hepatoma cells HepG2. Furthermore, it has been shown that strictly IL-6 dependent hybridoma cells do not proliferate in response to very low amounts of IL-6 when sIL-6R present in culture media is continuously removed.

Initially described as the interleukin-6 signal transducer, gp130 is a transducer chain shared by many cytokines, such as IL-6, IL-11, leukemia inhibitory factor (LIF), oncostatin M (OSM) and ciliary neurotrophic factor (CNTF). All of these cytokines act via a bi- or tripartite receptor complex in which signalling is triggered by homodimerization (for IL-6) or heteradimerization with LIF-Rb/gp130 protein (for IL-11, LIF, OSM and CNTF) of gp130. These cytokines thus mediate similar biologic activities in various tissues.

While gp130 can be found on nearly all cell types, the IL-6R shows a much more restricted expression. The release of sIL-6R by one cell type renders other cells, which only express gp130 responsive to IL-6. This scenario is called trans-signalling. Indeed, several cellular activities have been described which require the complex of sIL-6R and IL-6 and are not seen with IL-6 alone. Soluble gp30 protein is found in high concentrations in human plasma. Recently the designer-cytokine hyper-LL-6 (H-IL-6), in which the C-terminus of sIL-6R is covalently fused to the N-terminus of mature IL-6 by a flexible peptide linker, has been described. As seen with the complex of IL-6/sIL-6R, H-IL-6 also acts on cells which only express gp130. In contrast to the separate components IL-6 and sIL-6R, a 100 to 1000 lower concentration of this fusion molecule is sufficient to induce comparable biological signals.

For the treatment of various diseases such as Crohn's disease etc. the specific blocking of IL-6 responses dependent on soluble IL-6R might be desirable for treatment. Unfortunately, the compounds available so far for this purpose are characterized by several disadvantages like low production rate, high clearance rate, low half life, etc.

Thus, the technical problem underlying the present invention was to provide means suitable for treating diseases where the specific blocking of IL-6 responses dependent on sIL-6R might have a beneficial effect that overcome the disadvantages of the means of the prior art.

SUMMARY OF THE INVENTION

The solution of the said technical problem is achieved by providing the embodiments characterized in the claims. During the experiments leading to the present invention it was found that a PEGylated soluble gp130-dimer efficiently inhibits the anti-apoptotic effect of sIL-6R from LPMC from Crohn's disease (CD) patients and that, thus, said compound is useful for the treatment of said disease and related diseases like, e.g., colitis or rheumatoid arthritis. Crohn's disease is a chronic inflammatory disease of the gastrointestinal tract which is characterised by frequently occurring relapses of acute inflammation. Inflammation associated with infection, injury, and other factors rapidly induces the acute-phase reaction (APR) which is characterized by the production of acute-phase proteins (APPs). The APR mainly results in an increase of vascular permeability and fever. APPs can be distinguished into two different groups depending on the cytokine that regulates their expression and activation. IL-6 family cytokines upregulate the expression of type-II APP genes which is mediated by STAT3 activation. IL-6 also contributes to the increase in type-I APP levels, which are mainly regulated by IL-1. Strong STAT3 activation (i.e. tyrosine phosphorylation) has been described in colonic tissues from IBD patients. Moreover, STAT3 activation was significantly reduced in IL-6 KO mice, which was accompanied by a reduced development of experimental colitis in these mice (Suzuki et al., J Exp Med, 2001, 193:471). These findings indicate that IL-6/IL-6R-mediated STAT3 activation plays a central role in the development and perpetuation of colitis. In another inflammatory disease, rheumatoid arthritis (RA), STAT3 was shown to be important for the survival of RA synovial fibroblasts (Krause et al., J Immunol, 2002, 169:6610). It was therefore suggested that STAT3 may represent a good target for gene therapy. Constitutive STAT3 activation is also known to be a "cancer-causing" factor and is e.g. accompanied with the upregulation of anti-apoptotic proteins such as Bcl-2 or Bcl-XL (Turkson et al., Oncogene, 2000, 19:6613). It was found that the PEGylated soluble gp130-dimer significantly reduced the activity of STAT3. Furthermore, it was found that the efficiency of sgp130PEG was significantly higher than that of sgp130Fc of EP 00 108 691.7 in reducing IL-6/IL-6R/gp130-mediated signal transduction processes and disease parameters. Additionally the halflife of sgp130PEG was approximately 2-fold higher than that of the sgp130Fc molecule. Furtheron, a lower dose of sgp130PEG could be used in therapeutic approaches to obtain the same results as with sgp130Fc. Consequently, these results of sgp130PEG mean lower side-effects, lower exposure of the patients, reduced application frequence and lower therapeutic costs.

BRIEF DESCRIPTION OF FIGURES

FIG. 2 Nucleotide sequence and corresponding encoded protein sequence of the first three extracellular domains (D1-D3) of human gp130 (sgp130 (D1-D3)).

FIG. 3 Nucleotide sequence and corresponding encoded protein sequence of human herpesvirus 8 (HHV8)-derived viral interleukin-6 (vIL-6).

FIG. 4 Analysis of apoptosis in lamina propria mononuclear cells (LPMC) from Crohn's disease patients LPMC were isolated and cultured as described in Example 1 for 48 hours in the presence or absence of 10 μg/ml each of neutralizing anti-IL-6 antibody, sgp130Fc and sgp130PEG. Apoptosis was determined by staining of the cells with Annexin V and propidium iodide and subsequent FACS analysis. The percentage of apoptotic (Annexin V positive and propidium iodide negative) cells is depicted.

FIG. 7 Nucleotide sequence and corresponding protein sequence of the first three extracellular domains (D1-D3) of human gp130 (sgp130(D1-D3).1).

FIG. 8 A) analysis of apoptosis in lamina propria mononuclear cells (LPMC) from Crohn's disease patients. LPMC were isolated and cultured as described in Example 1 for 48 hours in the presence or absence of 10 μg/ml each of neutralizing anti-IL-6 antibody, sgp130Fc and sgp130PEG. Apoptosis was determined by staining of the cells with annexin V and propidium iodide and subsequent FACS analysis. The percentage of apoptosic (Annexin V positive and propidium iodide negative) cells is depicted. B) The same experiment as described under 4A was performed except that sgp130dimer or sgp130TagPEG were used instead of anti-IL-6 antibody, sgp130Fc and sgp130PEG.

FIG. 9 Proliferation of BAF/gp130 cells in response to (A) 5 ng/ml of hyper-IL-6 (H-IL-6) or (B) 100 ng/ml IL-6+50 ng/ml sIL-6R and increasing amounts of either sgp130TagPEG or sgp130dimer. Proliferation was determined by detecting [3H]-thymidine incorporation in a scintillation counter.

Figure 1:
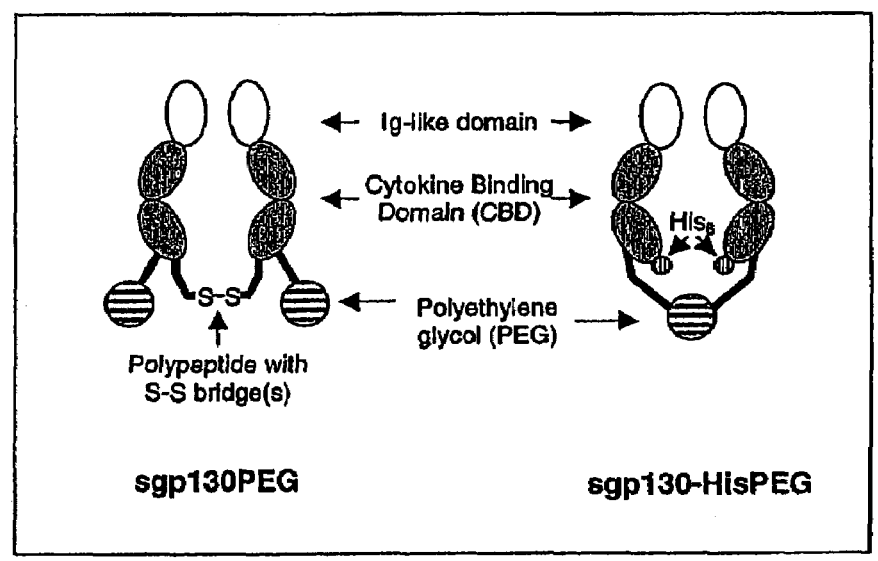
FIG. 1 Schematic drawing of sgp130PEG and sgp130 His-PEG.

Thus, the present invention relates to a polypeptide-dimer comprising two soluble gp130 molecules, wherein at least one, preferably both, of said soluble gp130 molecules is (are) covalently linked to polyethylene glycol.

DETAILED DESCRIPTION OF THE INVENTION

The polypeptide-dimers of the present invention may be engineered using known methods. The term "soluble" as used herein refers to a gp130 molecule lacking the intracellular domain and, preferably, the transmembrane domain. The domains utilised may consist of the extracellular domains D1-D3 of gp130 or they may consist of mutants or fragments thereof that maintain the ability to inhibit the activity of the agonistic complex IL-6/sIL-6R. PEGylation of the sgp130 molecules can be carried, e.g., according to the methods described for human IFN-γ, IFN-α, IFN-β, IL-15 or IL-2 (Tang et al., Sheng Wu Hua Xue Yu Sheng Wu Wu Li Xue Bao (Shanghai), (1996), 28:312; Youngster et al., Curr Pharm Des (2002), 8:2139; Grace et al., J Interferon Cytokine Res (2001), 21:1103; Pepinsky et al., J Pharmacol Exp Ther (2001), 297:1059; Pettit et al., J Biol Chem (1997), 272:2312; Goodson et al. Biotechnology NY (1990), 8:343; Katre; J Immunol (1990), 144:209). Preferably, the polypeptide corresponding to the soluble part of gp130 is the only biologically active polypeptide of the polypeptide-dimer of the present invention, i.e. does not contain further polypeptide moieties like an Fc-domain and/or fibronectin(FN)III.

In a preferred embodiment, the polypeptide-dimer of the present invention is characterized in that at least one of said two soluble gp130 molecules comprises the amino acid sequence as depicted in FIG. 2 or 3.

In a more preferred embodiment, the polypeptide-dimer of the present invention is characterized in that both of said two soluble gp130 molecules comprise the amino acid sequence as depicted in FIG. 2 or 3.

Any kind of polyethylene glycol is suitable for the present invention provided that the PEG-polypeptide-dimer is still capable of blocking IL-6 responses dependent on sIL-6R which can be assayed according to methods known in the art, e.g., the method described in Example 1. Preferably, the polyethylene glycol of the polypeptide-dimer of the present invention is PEG 1000, 2000, 3000, 5000, 10000, 15000, 20000 or 40000 with PEG 20000 or 40000 being particularly preferred.

In order to form the dimer the two soluble gp130 molecules are linked to each other via one or more disulfid bridges. This can be achieved, e.g., by recombinant expression, wherein the nucleic acid sequence encoding sgp130 contains one or more cystein residues encoding codons between the stop-codon and the codon encoding the C-terminal amino acid residue of sgp130. Alternatively, for generating the dimer one may employ a flexible linker domain, preferably fusing the monomers together in tandem ("tail-to-tail"). This linker may be entirely artificial (e.g., polyglycine repeats which may be interrupted by serine, alanine and/or threonine at a certain interval) or "borrowed" from naturally occurring proteins, such as the hinge region of human IgG. Additionally, the molecules of the dimer may be tagged e.g. by His-His-His-His-His-His (His6), FLAG, Strep-Tag, green fluorescence protein (GFP), c-myc, glutathione S-transferase (GST), HA, calmodulin-binding peptide (CBP) or other epitopes to which antibodies are available, to allow rapid purification by suitable chromatography systems, detection e.g. by Western blotting or ELISA, immunoprecipitation, or activity depletion/ blocking in bioassays.

In a further alternative embodiment, the two soluble gp130 molecules are linked to each other through "forked" PEGs which comprise at least one PEG and two reactive groups at a precise distance apart.

A variety of means can be used to generate and identify mutations of sgp130 that have the desired properties. Random mutagenesis by standard methods of the DNA encoding sgp130 may be used, followed by analysis of the collection of products to identify mutated cytokines having the desired properties. Mutagenesis by genetic engineering has been used extensively in order to elucidate the structural organisation of functional domains of recombinant proteins. Several different approaches have been described in the literature for carrying out deletion or substitution mutagenesis. The most successful appear to be alanine scanning mutagenesis (Cunningham and Wells, Science 244 (1989), 1081-1085) and homolog-scanning mutagenesis (Cunningham et al., Science 243 (1989), 1330-1336).

The polypeptides of the present invention are preferably recombinantly produced by use of a polynucleotide encoding a polypeptide of the present invention and vectors, preferably expression vectors containing said polynucleotides. For the production of the polypeptides of the invention, the polynucleotides are obtained from existing clones, i.e., preferably encode the naturally occurring polypeptide or a part thereof. Polypeptides encoded by any polynucleotide which hybridises to the complement of the native DNA or RNA under highly stringent or moderate stringent conditions (for definitions, see Sambrook, Molecular Cloning A Laboratory Manual, Cold Spring Harbor Laboratory (1989) N.Y.) as long as that polypeptide maintains the biological activity of the native sequence, are also useful for producing the polypeptide(s) of the present invention.

The recombinant vectors can be constructed according to methods well known to the person skilled in the art; see, e.g., Sambrook, Molecular Cloning A Laboratory Manual, Cold Spring Harbor Laboratory (1989) N.Y. A variety of expression vector/host systems may be utilised to contain and express sequences encoding the sgp130 polypeptides of the present invention. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector-enhancers, promoters, 5' and 3' untranslated regions which interact with host cellular proteins to carry out transcription and translation. Such elements may vary in their strength and specificity. Depending on the vector system and host utilised, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla, Calif.) or pSport1™ plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding the spg130 polypeptides, vectors based on SV40 or EBV may be used with an appropriate selectable marker.

In bacterial systems, a number of expression vectors may be selected depending upon the use intended for the polypeptide dimer of the present invention. Vectors suitable for use in the present invention include, but are not limited to the pSKK expression vector for expression in bacteria.

In the yeast, Saccharomyces cerevisiae, a number of vectors containing constitutive or inducible promoters such as alpha factor, alcohol oxidase, and PGH may be used; for reviews, see Grant et al. (1987) Methods Enzymol. 153:516-544.

In cases where plant expression vectors are used, the expression of sequences encoding the antibody of the present invention may be driven by any of a number of promoters. For example, viral promoters such as the 35S and 19S promoters of CaMV may be used alone or in combination with the omega leader sequence from TMV (Takamatsu, N. (1987) EMBO J. 6:307-311). Alternatively, plant promoters such as the small subunit of RUBISCO or heat shock promoters may be used (Coruzzi, G. et al. (1984) EMBO J. 3:1671-1680; Broglie, R. et al. (1984) Science 224:838-843; and Winter, J. et al. (1991) Results Probl. Cell Differ. 17:85-105). These constructs can be introduced into plant cells by direct DNA transformation or pathogen-mediated transfection. Such techniques are described in a number of generally available reviews (see, for example, Hobbs, S. and Murry, L. E. in McGraw Hill Yearbook of Science and Technology (1992) McGraw Hill, New York, N.Y.; pp. 191-196.

An insect system may also be used to express the sgp130 molecules of the present invention. For example, in one such system, Autographa californica nuclear polyhedrosis virus (AcNPV) is used as a vector to express foreign genes in Spodoptera frugiperda cells or in Trichoplusia larvae. The sequences may be cloned into a non-essential region of the virus, such as the polyhedrin gene, and placed under control of the polyhedrin promoter. Successful insertion of the gene encoding sgp130 will render the polyhedrin gene inactive and produce recombinant virus lacking coat protein. The recombinant viruses may then be used to infect, for example, S. frugiperda cells or Trichoplusia larvae in which APOP may be expressed (Engelhard, E. K. et al. (1994) Proc. Nat. Acad. Sci. 91:3224-3227).

In mammalian host cells, a number of viral-based expression systems may be utilised. In cases where an adenovirus is used as an expression vector, sequences encoding the polypeptide(s) of the present invention may be ligated into an adenovirus transcription/translation complex consisting of the late promoter and tripartite leader sequence. Insertion in a non-essential E1 or E3 region of the viral genome may be used to obtain a viable virus which is capable of expressing the antibody in infected host cells (Logan, J. and Shenk, T. (1984) Proc. Natl. Acad. Sci. 81:3655-3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation. Such signals include the ATG initiation codon and adjacent sequences. In cases where sequences encoding the sgp130, its initiation codon, and upstream sequences are inserted into the appropriate expression vector, no additional transcriptional or translational control signals may be needed. However, in case where only coding sequence is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125-162).

In addition, a host cell strain may be chosen for its ability to modulate the expression of the inserted sequences or to process the expressed polypeptide chains in the desired fashion. Post-translational processing which cleaves a "prepro" form of the polypeptide may also be used to facilitate correct insertion, folding and/or function. Different host cells which have specific cellular machinery and characteristic mechanisms for post-translational activities (e.g., CHO, HeLa, MDCK, HEK293, and W138), are available from the American Type Culture Collection (ATCC; Bethesda, Md.) and may be chosen to ensure the correct modification and processing of the foreign polypeptide chains.

For long-term, high-yield production of recombinant polypeptides, stable expression is preferred. For example, cell lines which stably express sgp130 chains may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

After the introduction of the recombinant vector(s), the host cells are grown in a selective medium, which selects for the growth of vector-containing cells. Any number of selection systems may be used to recover transformed cell lines. These include, but are not limited to, the herpes simplex virus thymidine kinase (Wigler, M. et al. (1977) Cell 11:223-32) and adenine phosphoribosyltransferase (Lowy, I. et al. (1980) Cell 22:817-23) genes which can be employed in tk.sup.- or aprt.sup.-cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567-70); npt, which confers resistance to the aminoglycosides neomycin and G-418 (Colbere-Garapin, F. et al (1981) J. Mol. Biol. 150:1-14) and als or pat, which confer resistance to chlorsulfuron and phosphinotricin acetyltransferase, respectively (Murry, supra). Additional selectable genes have been described, for example, trpB, which allows cells to utilise indole in place of tryptophan, or hisD, which allows cells to utilise histinol in place of histidine (Hartman, S. C. and R. C. Mulligan (1988) Proc. Natl. Acad. Sci. 85:8047-51). Recently, the use of visible markers has gained popularity with such markers as anthocyanins, beta-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121-131).

Purification of the recombinant polypeptides is carried out by any one of the methods known for this purpose, i.e., any conventional procedure involving extraction, precipitation, chromatography, electrophoresis, or the like. A further purification procedure that may be used is affinity chromatography using monoclonal antibodies which bind the target polypeptide and which are produced and immobilized on a gel matrix contained within a column. Impure preparations containing the recombinant polypeptide are passed through the column. The polypeptide will be bound to the column by the specific antibody while the impurities will pass through. After washing the polypeptide is eluted from the gel by a change in pH or ionic strength and then, if it is produced as the monomer, dimerized and PEGylated.

Accordingly, the present invention also relates to a method of producing the polypeptide-dimer of the present invention, comprising culturing a host cell transformed with a DNA sequence encoding a monomer of said polypeptide, recovering the polypeptide-monomer or dimer from said host cell or the culture and PEGylating the monomers or dimers.

The polypeptide-dimers of the present invention are useful in the treatment and/or prevention of all the pathologies, in which the activity of the agonistic complex IL-6/sIL-6R must be inhibited. For example, therapeutic uses of the polypeptide-dimers of the present invention would include the following:

(a) IL-6 appears to be directly involved in multiple myeloma by acting in either an autocrine or paracrine fashion to promote tumour formation. Furthermore, the elevated IL-6 levels create undesirable secondary effects such as bone resorption, hypercalcemia and cachexia. In these cases it is known that sIL-6R sensitises target cells for IL-6. Therefore, the polypeptide-dimers of the invention as described herein would be beneficial for both the secondary effects as well as for inhibiting tumour growth.

(b) In autoimmune diseases: the pathogenic significance of IL-6 in autoimmune disorders has been reviewed by many authors in the literature (see, e.g., Yoshizaki et al., Semin. Immunol. 4(3) (1992), 155-166), thus, interference with IL-6 signal transduction may be useful for autoimmune disease therapy (Nishimoto et al., Intern. Med. 38(2) (1999), 178-182). Examples of such pathologies are systemic lupus erythematosus, Hashimoto's thyroiditis, scleroderma, rheumatoid arthritis, multiple sclerosis, Autoimmune epithelitis, Diabetes mellitus, Sjögren's syndrome, polymyositis, glomerulonephritis and other inflammatory diseases, such as psoriasis and Crohn's disease.

(c) In osteoporosis, which can be exacerbated by lowering of estrogen levels in post-menopausal women or through ovariectomy, IL-6 appears to be a critical mediator of osteoclastogenesis, leading to bone resorption. Importantly, IL-6 only appears to play a major role in the estrogen-depleted state, and apparently is minimally involved in normal bone maintenance. Consistent with this, experimental evidence indicates that function-blocking antibodies to IL-6 can reduce the number of osteoclasts. While estrogen replacement therapy is also used, there appear to be side effects that may include an increased risk of endometrial and breast cancer. Thus, the polypeptide dimers of the present invention would be more specific to reduce osteoclastogenesis to normal levels.

(d) IL-6 may be a mediator of tumour necrosis factor (TNF) that leads to cachexia associated with AIDS and cancer, perhaps by reducing lipoprotein lipase activity in adipose tissue. Accordingly, the polypeptide-dimers of the invention described herein would be useful in alleviating or reducing cachexia in such patients.

(e) Bacterial and viral infections: the presence of Human Herpes Virus 8 (HHV8) has been demonstrated in more than 91% of Kaposi's sarcoma (KS) lesions. Moreover, the virus has been identified in primary effusion lymphoma (PEL) and in patients with multicentric Castleman disease (MCD). Intriguingly, bone marrow dendritic cells from multiple myeloma (MM) patients were shown to be infected by HHV8. Since then, the association of HHV8 with MM has been a subject of fierce debate, which was recently revived. The genome of HHV8 codes for several proteins with significant homologies to human anti-apoptotic proteins, chemokines, and cytokines including a vital form of Interleukin-6 (vIL-6) with 25% homology to human IL-6. vIL-6 has been demonstrated to have biologic activities reminiscent of human IL-6, i.e. stimulation of proliferation of murine hybridoma and human myeloma cells. More recently it was shown in mice, injected with vIL-6 transfected NIH3T3 cells, that viL-6 induced angiogenesis and hematopoiesis. It was concluded that through these functions vIL-6 played an important role in the pathogenesis of HHV8-associated disorders. The contribution of the IL-6R to vIL-6 signalling has been discussed controversially. One group using unpurified supernatants of vIL-6 transfected COS-7 cells has shown that STAT activity was induced in cells expressing gp130 but no IL-6R. In contrast, another group found that the activity of vIL-6 was reduced by an IL-6 receptor antagonist, arguing for an involvement of IL-6R in vIL-6 signalling.

Thus, the present invention also relates to a pharmaceutical composition containing an effective amount of a polypeptide-dimer of the present invention, preferably combined with a pharmaceutically acceptable carrier. "Pharmaceutically acceptable" is meant to encompass any carrier, which does not interfere with the effectiveness of the biological activity of the active ingredient and that is not toxic to the host to which it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at an effective dose.

An "effective amount" refers to an amount of the active ingredient that is sufficient to affect the course and the severity of the disease, leading to the reduction or remission of such pathology.

An "effective dose" useful for treating and/or preventing these diseases or disorders may be determined using methods known to one skilled in the art (see for example, Fingl et al., The Pharmacological Basis of Therapeutics, Goodman and Gilman, eds. Macmillan Publishing Co., New York, pp. 1-46 ((1975)).

Administration of the suitable compositions may be effected by different ways, e.g. by intravenous, intraperetoneal, subcutaneous, intramuscular, topical or intradermal administration. The route of administration, of course, depends on the kind of therapy and the kind of compound contained in the pharmaceutical composition. The dosage regimen will be determined by the attending physician and other clinical factors. As is well known in the medical arts, dosages for any one patient depends on many factors, including the patient's size, body surface area, age, sex, the particular compound to be administered, time and route of administration, the kind of therapy, general health and other drugs being administered concurrently.

Preferred medical uses of the polypeptide-dimers of the present invention described above are the treatment/prevention of bone resorption, hypercalcemia, cachexia, tumours, autoimmune diseases such as Crohn's disease and bacterial or viral infections.

The below examples explain the invention in more detail.

EXAMPLE 1

Material and Methods (A) Materials
DMEM, RPMI-1640, penicillin, streptomycin and gentamycin were purchased from Gibco (Eggenstein, Germany). FCS was obtained from Biochrom (Berlin, Germany). DEAE-Dextran was from Sigma (Taufkirchen, Germany). Restriction enzymes, T4-DNA ligase and Polynucleotide Kinase were from New England Biolabs (Schwalbach, Germany). [3H]-thymidine, ECL-reagents and X-ray films were obtained from Amersham Bioscience (Freiburg, Germany). The QuikChange Site-directed mutagenesis kit was from Stratagene (Amsterdam, NL). Antibodies were purchased from Cell Signalling Technology (Frankfurt, Germany). BAF/gp130 cells, recombinant IL-6 and hyper-IL-6 (H-1 L-6), a fusion protein comprising IL-6+sIL-6R (Rakemann et al., J. Biol. Chem. 274 (1999), 1257) were obtained from Stefan Rose-John (Director of the Institute of Biochemistry, Kiel, Germany). Human sgp130Fc was produced as described (Atreya et al., Nat. Med. 6 (2000), 583).

(B) Culture and Transfection of Cells
BAF/gp130 cells were grown in DMEM at 37° C., 5% $CO_2$ in a water saturated atmosphere. Cell culture media were supplemented with 10% FCS, 100 mg/l of streptomycin and 60 mg/l of penicillin. BAF/gp130 cells were cultured in the presence of 10 ng/ml of H-IL-6.

(C) Construction of sgp130 (D1-D3) and sgp130 (D1-D3) His Expression Plasmids
Cloning of the ligand binding domains of gp130 (D1-D3) was performed by amplifying the coding sequence of gp130 from base 1 to 978 (corresponding to amino acids Met 1 to Pro 326 (FIG. 2)) by PCR according to standard protocols. pSVL-sgp130-Fc (Atreya et al., Nat. Med. 6 (2000), 583) was taken as template. The resulting DNA fragment was purified on a 1% agarose gel, isolated by using a Qiagen MiniElute kit and cloned into the expression plasmids pQE60, pQE70 (Qiagen), pBAD/Myc-His (Invitrogen), pET-3, pET-11, pCAL-c and pCAL-kc (Stratagene). All constructs were identified by restriction digests and the inserts were sequence verified by standard techniques.

(D) Construction of sgp130 (D1-D3) $P_n$ Expression Plasmids
Polypeptides of different lengths ($P_n$) containing one or more cystein residues were added to the C-terminus of sgp130 (D1-D3) by site-directed mutagenesis according to the standard cloning techniques. All constructs were identified by restriction digests and the inserts were sequence verified.

(E) Construction of vIL-6-His Expression Plasmids
The cDNA for vIL-6 was amplified by PCR (coding sequence in FIG. 3) by using freshly isolated human genomic DNA as template. For expression of vIL-6-His in COS-7 cells the viL-6 cDNA was inserted into the mammalian expression plasmids pEF11myc-His, pUB6N5-His (Invitrogen) or pQE-TriSystem (Qiagen) in front of a polyhistidine (His) tag. For expression of vIL-6-His in bacteria vIL-6 cDNA was inserted into a prokaryotic expression vector (pQE60, pQE70 (Qiagen), pBAD/Myc-His (Invitrogen), pET-3, pET-11, pCAL-c or pCAL-kc (Stratagene)) in front of a polyhistidine tag. All constructs were identified by restriction digest and the inserts were sequence verified by standard techniques.

(F) Purification of viL-6-His
Recombinant viL-6-His was purified as described by Müllberg et al.; J. Immunol. 164 (2000), 4672).

(G) Purification of sgp130 (D1-D3)-$P_n$ (Method 1)
Purified recombinant vIL-6-His was bound to a Ni-NTA agarose column (Qiagen) as follows: The column material was equilibrated with 5 bed volumes of 50 mM phosphate buffer (pH 7.5), 500 mM NaCl, and 20 mM imidazole (Equilibration Buffer, EB). vIL-6-His was loaded onto the column and unbound protein was removed by washing with 5 bed volumes of EB. A protein suspension containing sgp130 (D1-

D3)-$P_n$ was loaded onto the column and the column was subsequently washed with 10 bed volumes of EB. Finally sgp130 (D1-D3)-$P_n$ was eluted with a citrate buffer (pH 1.4) and the eluate was immediately neutralized. The eluate was purified by mono-Q fast protein liquid chromatography (Pharmacia) and dialyzed against PBS.

(H) Purification of sgp130 (D1-D3)-$P_n$ (Method 2)

Prokaryotic expression plasmids encoding sgp130 (D1-D3)-$P_n$ and vIL-6-His were cotransfected into bacterial strains TOP10 (Invitrogen), XL1-Blue, BL21(DE3) (Stratagene), M15 [pREP4] or SG13009 [pREP4] (Qiagen). 24 hours after transformation, the protein production was started with 1 mM isopropyl-β-D-hiogalactopyranoside (IPTG) and the proteins were extracted 6 hours later. The protein extract was loaded onto a Ni-NTA agarose column which was beforehand equilibrated with 5 bed volumes of EB. Unbound proteins were removed by washing the column with 10 bed volumes of EB. gp130 (D1-D3)-$P_n$ was finally eluted, purified and dialyzed as described above.

(I) Purification of sgp130 (D1-D3)-His sgp130 (D1-D3)-His was purified by the same technique as described for vIL-6-His.

(J) PEGylation of sgp130 (D1-D3)-$P_n$

During the last years an increasing interest is arising for the covalent modification of biological macromolecules by polyethylene glycol (PEG). This kind of modification is extremely important for pharmaceutical and biotechnological applications. PEGylation (the covalent attachment of PEG) leads for example to shielding of antigenic or immunogenic epitopes. Moreover, it reduces receptor-mediated uptake by the reticuloendothelial system or prevents recognition and degradation by proteolytic enzymes (5). PEGylation of proteins has been shown to increase their bioavailability by reducing the renal filtration. sp130 (D1-D3) contains 9 cystein (C) residues with 8 of them being involved in disulfide bridges ($C_{28}$-$C_{54}$, $C_{48}$-$C_{103}$, $C_{134}$-$C_{144}$, $C_{172}$-$C_{182}$). The last $C_{301}$ contains a free sulfhydryl group and is therefore suitable for site-specific PEGylation. The modification of sgp130 (D1-D3) was exerted by adding a 3-fold molar excess of mPEG-MAL, MW 20.000 (Nektar Therapeutics, San Carlos, Calif., USA) to sgp130 (D1-D3)-$P_n$ at pH 7.2. The reaction was performed for 60 minutes at room temperature and the product was isolated by a final gel filtration step according to standard conditions.

PEGylated sgp130 (D1-D3)-His was produced by incubating the protein with a 3-fold molar excess of forked mPEG $(MAL)_2$, MW 20.000 (Nektar) at pH 7.2 at room temperature for 90 minutes. The product was subsequently gel filtrated according to standard techniques.

(K) Isolation and Stimulation of Lamina Propria Mononuclear Cells (LPMC)

LPMC were cultured in complete medium consisting of RPMI-1640 with 3 mM L-glutamine, 10 mM HEPES buffer, 10 μg/ml gentamycin, 100 U/ml penicillin, 100 U/ml streptomycin, 50 μM 2-mercaptoethanol and 10% heat-inactivated FCS. Cells were stimulated with 10 μg/ml C reactive protein (Sigma), 50 ng/ml phorbol-12-myristate-13-acetate (PMA) and 10 μg/ml phytohaemagglutimin (PHA) (Sigma) in the presence or absence of sgp130Fc, neutralising IL-6R specific antibody (provided by Professor Dr. Rose-John, University of Kiel, Germany), sgp130PEG or sgp130TagPEG at concentrations at 1 to 10 μg/ml as indicated in the Figures. After 48 hours cells were stained with Annexin V and propidium iodide using the ApoAlert Annexin V-FITC Apoptosis Detection Kit (BD Bioscience, Heidelberg, Germany) and analysed by FACS.

(L) Proliferation Assays

BAF/gp130 cells were extensively washed with PBS in order to remove growth factors and resuspended in cytokine free medium. $5 \times 10^3$ cells per well of a 96-well plate were cultured in a final volume of 100 μl with cytokines and increasing amounts of sgp130Fc or sgp130PEG or sgp130TagPEG as indicated in the Figures for 68 hours and subsequently pulse labelled with 0.25 mCi [$^3$H]-thymidine for 4 hours. Cells were harvested on glass filters and incorporated [$^3$H]-thymidine was determined by scintillation counting.

(M) Luciferase Reporter Gene Assay

BAF31gp130 cells were cotransfected with the reporter gene plasmids pSTAT3-TA-Luc (BD Bioscience, Heidelberg, Germany) and pCMV-Luc and incubated for 24 hours. The transfected cells were then incubated with 5 ng/ml of H-IL-6 in the absence or presence of 10 μg/ml sgp130Fc, sgp130PEG or sgp130TagPEG, respectively, for another 20 hours. Extraction and detection of luciferase activity was performed by using the Dual Luciferase Reporter Gene Assay from Promega (Mannheim, Germany) according to the manufacturers manual and measurement in a MicroLumatPlus LB96V microplate luminometer (EG&G Berthold, Wellesley, Mass., USA).

(N) Construction of sgp130 (D1-D3).1 and sgp130 (D1-D3)-Tag expression plasmids

Cloning of the ligand binding domains of gp130 (D1-D3).1 was performed by amplifying the coding sequence of gp130 from base 70 to 966 (corresponding to aminoacids Leu 24 to Tyr 322 (FIG. 2)) by PCR according to standard protocols. pSVL-sgp130-Fc (2) was taken as template. The resulting DNA fragment was purified on a 1% agarose gel, isolated by using a Qiagen MiniElute kit and cloned into an appropriate expression plasmid. For the tagged protein expression vectors comprising the appropriate tag such as His($_{4-6}$), FLAG, Step-Tag, GFP, GST, HA CBP or other epitopes to which antibodies are available were used. Alternatively, the desired tag was directly cloned behind the sgp130 (D1-D3).1 cDNA. All constructs were identified by restriction digest and the inserts were sequence verified by standard techniques.

(O) Construction of sgp130-$P_n$ expression plasmids

Polypeptides of different length ($P_n$) containing one or more cystein residues were added to the C-terminus of sgp130 by site-directed mutagenesis of the corresponding expression plasmids according to the manufacturers manual. All constructs were identified by restriction digest and the inserts were sequence verified by standard techniques.

(P) Construction of vIL-6-His Expression Plasmids

The cDNA for vIL-6 was amplified by PCR (coding sequence in FIG. 3) by using freshly isolated human genomic DNA as template. For expression of vIL-6-His in COS-7 cells the vIL-6 cDNA was inserted into an appropriate mammalian expression plasmid in front of a polyhistidine (His) tag, e.g. pcDNA3.1/myc-His, pEF1/myc-His, pUB6/V5-His (Invitrogen), pQE-TriSystem (Qiagen) or others. For expression of vIL-6-His in bacteria vIL-6 cDNA was inserted into an appropriate prokaryontic expression vector in front of a polyhistidine tag, e.g. pQE60, pQE70 (Qiagen), pBAD/Myc-His (Invitrogen), pET-3, pET-11, pCAL-c, pCAL-kc (Stratagene) or others. All constructs were identified by restriction digest and the inserts were sequence verified by standard techniques.

(Q) Purification of sgp130-$P_n$ Method I

Viral Interleukin-6 (vIL-6) (4) has been shown to specifically bind to gp130 without further need of the IL-6 receptor (IL-6R) (3). This interaction of vIL-6 was used to purify sgp130 by a vIL-6-His affinity column. Purified recombinant vIL-6-His was bound to a Ni-NTA agarose column (Qiagen)

as follows: The column material was equilibrated with 5 bed volumes of 50 mM phosphate buffer (pH 7.5), 500 mM NaCl, and 20 mM imidazole (Equilibration Buffer, EB). vIL-6-His was loaded onto the column and unbound protein was removed by washing with 5 bed volumes of EB. A protein suspension containing sgp130-P$_n$ was loaded onto the column and the column was subsequently washed with 10 bed volumes of EB. Finally sgp130-P$_n$ was eluted by a citrate buffer pH 1.4. The eluate was immediately neutralized, purified by mono-Q fast protein liquid chromatography (Pharmacia) and dialyzed against PBS.

(R) Purification of sgp130-P$_n$ (Method II)

Prokaryontic expression plasmids encoding gp130-P$_n$ and vIL-6-His were cotransfected into appropriate bacterial strains, e.g. TOP10 (Invitrogen), XL1-Blue, BL21(DE3) (Stratagene), M15 [pREP4], SG13009 [pREP4] (Qiagen) or others. 24 hours after transformation, the protein production was started with 1 mM isopropyl-β-D-thiogalactopyranoside (IPTG) and the proteins were extracted 6 hours later. The protein extract was loaded onto a Ni-NTA agarose column which was beforehand equilibrated with 5 bed volumes of EB. Unbound proteins were removed by washing the column with 10 bed volumes of EB. gp130-P$_n$ was finally eluted, purified and dialyzed as described before.

(S) Purification of sgp130Tag sgp130Tag (with Tag=His$_6$) was purified by the same technique as described for vIL-6-His. In case of another tag such as His$_{(4-6)}$, FLAG, Step-Tag, GFP, GST, HA CBP or other epitopes to which antibodies are available the sgp130Tag molecule was separated by a suitable antibody immobilized on a matrix such as agarose.

(T) PEGylation of sgp130

During the last years an increasing interest is arising for the covalent modification of biological macromolecules by polyethylene glycol (PEG). This kind of modification is extremely important for pharmaceutical and biotechnological applications. PEGylation (the covalent attachment of PEG) leads for example to shielding of antigenic or immunogenic epitopes. Moreover, it reduces receptor-mediated uptake by the reticuloendothelial system or prevents recognition and degradation by proteolytic enzymes (5). PEGylation of proteins has been shown to increase their bioavailability by reducing the renal filtration.

sp130 contains 9 cystein (C) residues with 8 of them being involved in disulfide bridges ($C_{28}$-$C_{54}$, $C_{48}$-$C_{103}$, $C_{134}$-$C_{144}$, $C_{172}$-$C_{182}$). The last $C_{30}$, contains a free sulfhydryl group and is therefore suitable for site-specific PEGylation. The modification of sgp130 was exerted by adding a 3-fold molar excess of MPEG-MAL, MW 20.000 (Nektar Therapeutics, San Carlos, Calif., USA) to sgp130-P$_n$ at pH 7.2. The reaction was performed for 60 minutes at room temperature and the product was isolated by a final gel filtration step according to standard conditions.

PEGylated sgp130Tag was produced by incubating the protein with a 3-fold molar excess of MPEG (MAL)$_2$, MW 20.000 at pH 7.2 at room temperature for 90 minutes. The product was subsequently gel filtrated according to standard techniques.

EXAMPLE 2 sgp130PEG and sgp130TagPEG Inhibit the Antiapoptotic Effect of sIL-6R on LPMC from Crohn's Disease (CD) Patients A neutralizing antibody directed against IL-6R was able to induce apoptosis in lamina propria T-cells from CD patients (Atreya et al., 2000). The effect of anti-IL-6R mAb was also demonstrated in three different models of colitis, i.e. scid mice reconstituted with CD62L$^+$ CD45RB$^{high}$ CD4$^+$ T cells, IL-10 deficient mice and trinitrobenzene sulphonic acid (TNBS) treated mice. In all cases the colitis activity was downregulated at a similar level to that observed after anti-TNF mAb treatment (Atreya et al., 2000). The goal of this experiment was to show whether the sgp130PEG and sgp130TagPEG of the present invention would have the same efficiency as, e.g., sgp130Fc in inducing apoptosis in LPMC.

LPMC were cultured in presence of neutralizing anti-IL-6R antibody, sgp130Fc, sgp130PEG or sgp130TagPEG under conditions described in Example 1. Apoptotic cells were determined as Annexin V positive, propidium iodide negative cells by FACS analysis. Untreated samples contained approximately 60% apoptotic cells whereas treatment with anti-IL-6 antibody, sgp130Fc, sgp130PEG or sgp130TagPEG resulted in an increase of apoptotic cells between 11% to 16%. An un-PEGylated sgp130dimer was less effective demonstrating the importance of PEGylation for the biological activity of the molecule (FIGS. 4 and 8).

EXAMPLE 3

Inhibition of IL-6/sIL-6R Dependent Proliferation of BAF/3 Cells

Figure 5:
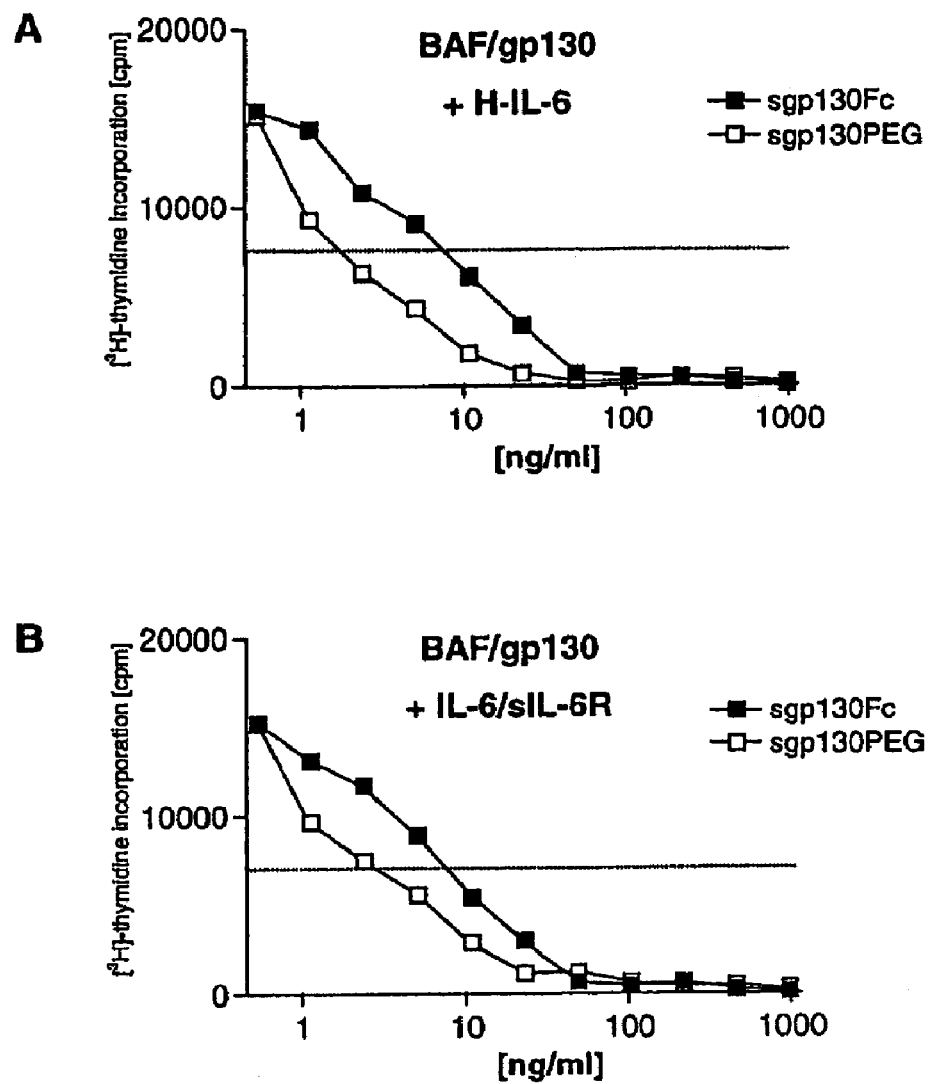
FIG. 5 Proliferation of BAF/gp130 cells in response to (A) 5 ng/ml of hyper-IL-6 (H-IL-6) or (B) 100 ng/ml IL-6+50 ng/ml sIL-6R and increasing amounts of either sgp130Fc or sgp130PEG proliferation was determined by detecting [3H]-thymidine incorporation in a scintillation counter.

The IL-3 dependent pre-B cell line BAF/3 does not express gp130 and is therefore not able to respond to IL-6 or IL-6/sIL-6R. In contrast, BAF/3 cells stably transfected with human gp130 cDNA (BAF/gp130) are able to grow in the absence of IL-3 in response to IL-6/sIL-6R or hyper-IL-6 (H-IL-6). BAF/gp130 simulated with either IL-6/sIL-6R (FIGS. 5A and 9A) or H-IL-6 (FIGS. 5B and 9B) were treated with increasing amounts of sgp130Fc, sgp130PEG or sgp130TagPEG and the effect of both sgp130 molecules on the proliferation of the cells was measured. In both experiments increasing amounts of sgp130Fc, sgp130PEG or sgp130TagPEG led to a significant reduction of [$^3$H]-thymidine incorporation. However, a half-maximal incorporation (dotted line at ~7.500 cpm) was reached when 7.5 to 10 ng/ml of sgp130Fc were given to the cells. In contrast, the same incorporation reduction was already seen with a concentration of sgp130PEG and sgp130TagPEG of 1 to 5 ng/ml. This indicates that sgp130PEG and sgp130TagPEG treatment was working at a factor of 1.5 to 3 better than sgp130Fc did. Additionally, in panel B un-PEGylated sgp130dimer was used to demonstrate the important role of PEGylation for the biological activity of the protein.

EXAMPLE 4 sgp130PEG Inhibits H-IL-6 Induced STAT3 Activation in BAF/gp130 Cells

Figure 6:
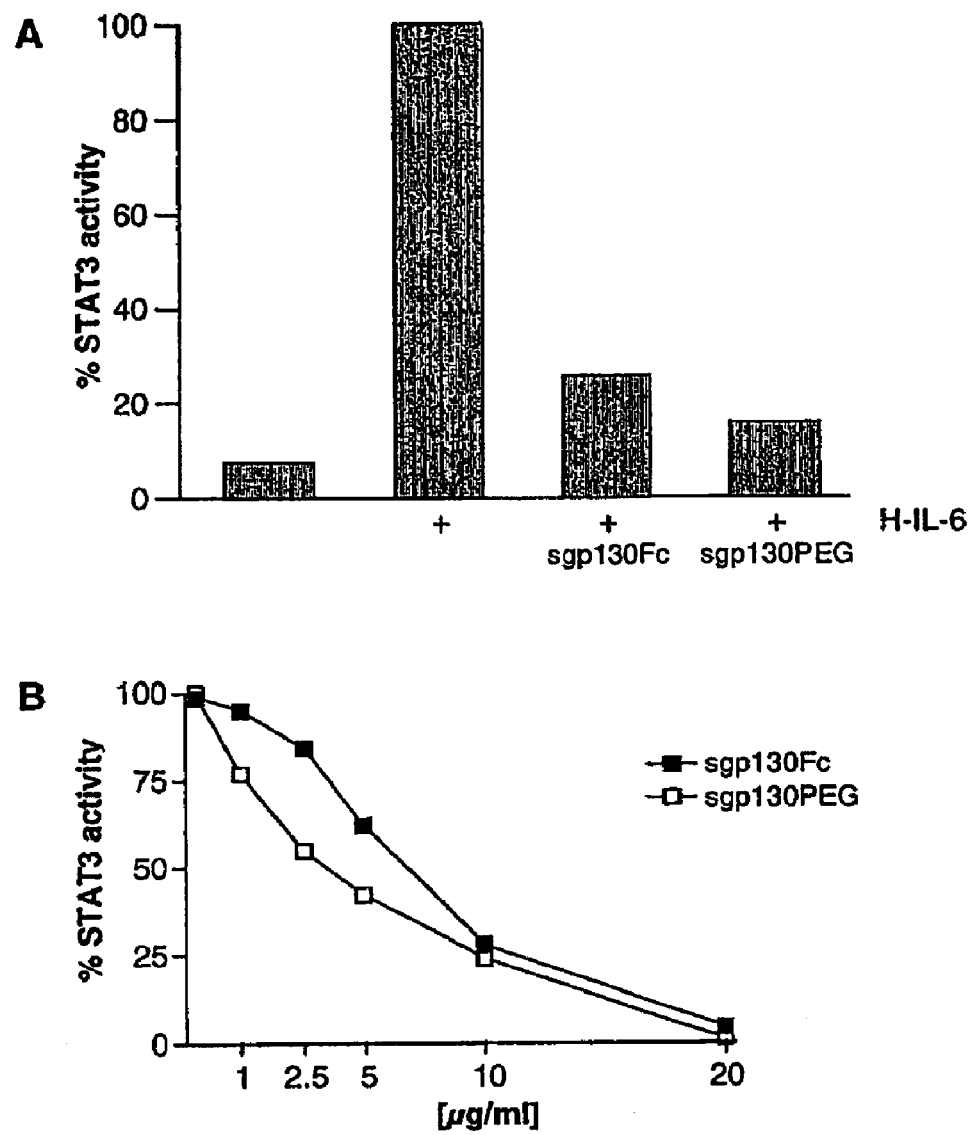
FIG. 6 A) Activation of a STAT3-driven reporter gene plasmid after H-IL-6 treatment and inhibition of STAT3 activity by sgp130Fc or sgp130PEG (10 μg/ml each). B) Concentration dependent downregulation of H-IL-6-induced STAT3 activation by either sgp130Fc or sgp130PEG.
Figure 10:
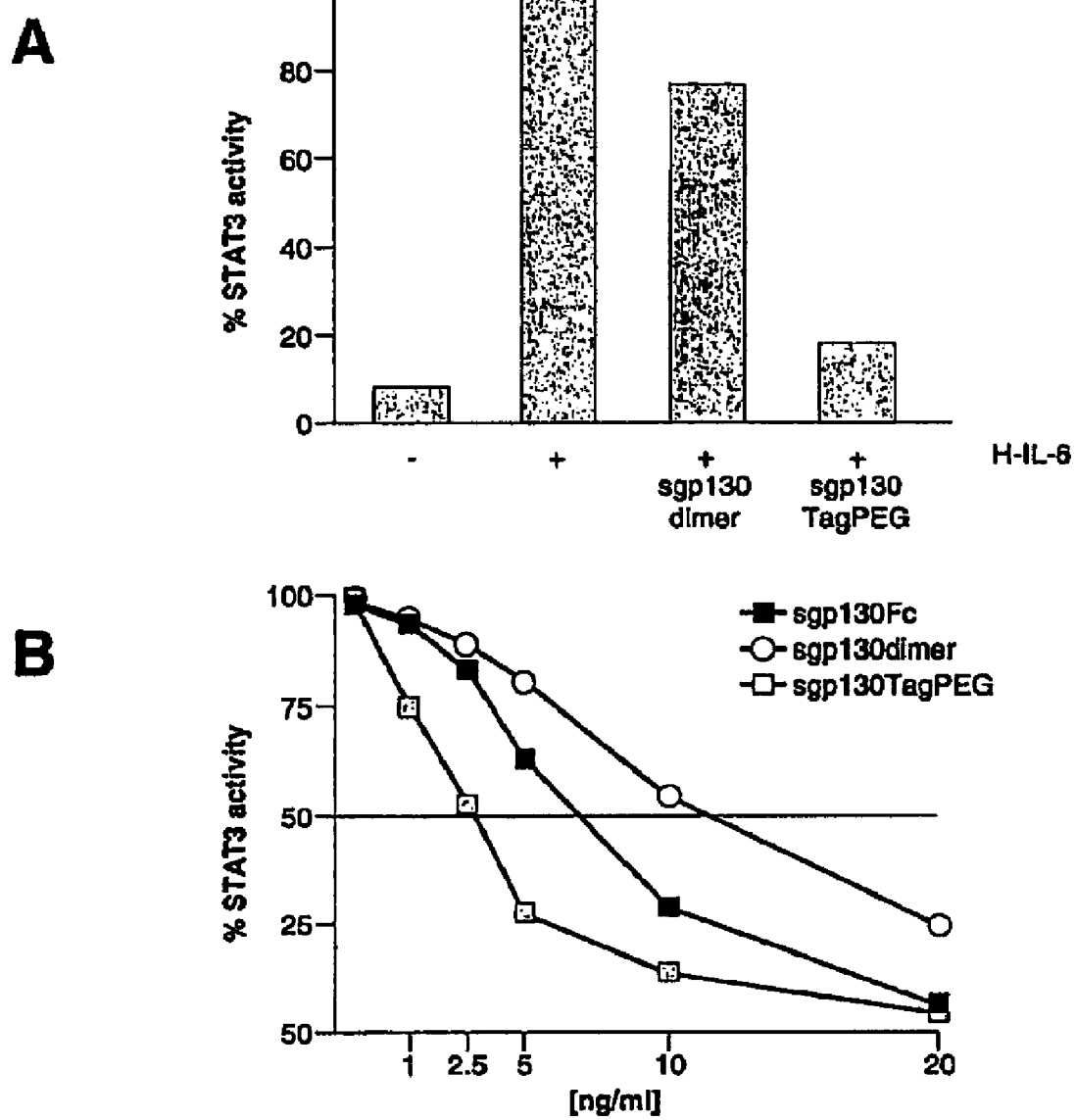
FIG. 10 A) Activation of a STAT3-driven reporter gene plasmid after H-IL-6 treatment and inhibition of STAT3 activity by sgp130 dimer or sgp130TagPEG (10 μg/ml each). B) Concentration dependent downregulation of H-IL-6-induced STAT3 activation by either sgp130dimer or sgp130TagPEG.

The latent cytoplasmic transcription factor signal transducer and activator of transcription (STAT)$_3$ is known to be activated in several different cell types by IL-6 treatment. The function of STAT3 has been intensively studied in different cell types. These include the induction of an acute-phase response in hepatoma cells, stimulation of proliferation in B lymphocytes, activation of terminal differentiation and growth arrestin monocytes, and maintenance of the pluripotency of embryonic stem cells (review in Levy and Lee, J. Clin. Invest. 109 (2002), 1143). To determine whether IL-6-induced STAT3 activation is influenced by sgp130PEG or sgp130TagPEG BAF/gp130 cells were transfected with pSTAT3-TA-Luc as described in Example 1. 24 hours later, the cells were treated with 5 ng/ml of H-IL-6 in the absence of or presence of 10 µg/ml of sgp130Fc, sgp130PEG or sgp130TagPEG respectively for another 20 hours. The cells were extracted and firefly luciferase activity was determined. Relative luciferase activity in cells treated solely with H-IL-6 was set to 100% (FIGS. 6A and 10A). In contrast, STAT3 activity was reduced to 26% (sgp130Fc), 18% (sgp130PEG) and 19% (sgp130TagPEG), respectively. In the second experiment the dose-dependence of the afore described effect was determined by treating the cells with increasing amounts of sgp130Fc, sgp130PEG or sgp130TagPEG respectively (FIGS. 6B and 10B). A half-maximal activation of STAT3 was determined with sgp130PEG and sgp130TagPEG at a concentration of 2.5 µg/ml whereas the same effect was seen with sgp130Fc at a concentration of approximately 7.5 µg/ml. Here again, as demonstrated before, the efficiency of sgp130PEG and sgp130TagPEG was approximately 2 to 3-fold higher than that observed with sgp130Fc.

What is claimed:

1. A polynucleotide encoding a polypeptide-dimer comprising two soluble gp130 molecules or a monomer of said dimer, wherein at least one of said soluble gp130 molecules is covalently linked to polyethylene glycol wherein each of said soluble gp130 molecules consists of extracellular domains D1-D3 of gp130 that maintain the ability to inhibit the activity of agonistic complex IL-6/sIL-6R, and wherein at least one of said two soluble gp130 molecules comprises the amino acid sequence of SEQ ID NO: 2.

2. An isolated expression vector comprising the polynucleotide of claim 1.

3. An isolated host cell comprising the expression vector of claim 2.

4. A method of producing the polypeptide-dimer of claim 3, comprising:

culturing said host cell;

recovering the polypeptide-monomer or dimer from said host cell or the culture; and PEGylating the monomers or dimers.

* * * * *